US009422375B2

(12) United States Patent
Christianson et al.

(10) Patent No.: US 9,422,375 B2
(45) Date of Patent: *Aug. 23, 2016

(54) NON-CYCLOPENTADIENYL-BASED CHROMIUM CATALYSTS FOR OLEFIN POLYMERIZATION

(71) Applicant: Dow Global Technologies LLC, Midland, MI (US)

(72) Inventors: Matthew D. Christianson, Midland, MI (US); Timothy S. De Vries, Midland, MI (US); Robert D J Froese, Midland, MI (US); Matthias S. Ober, Midland, MI (US); Jasson T. Patton, Midland, MI (US); Duane R. Romer, Midland, MI (US); Gordon R. Roof, Midland, MI (US); Lixin Sun, Sugar Land, TX (US); Endre Szuromi, Richwood, TX (US); Curt N. Theriault, Hemlock, MI (US); Dean M. Welsh, Midland, MI (US); Timothy T. Wenzel, Midland, MI (US); Paul H. Moran, Missouri City, TX (US)

(73) Assignee: Dow Global Technologies LLC

( * ) Notice: Subject to any disclaimer, the term of this patent is extended or adjusted under 35 U.S.C. 154(b) by 0 days.

This patent is subject to a terminal disclaimer.

(21) Appl. No.: 14/931,258

(22) Filed: Nov. 3, 2015

(65) Prior Publication Data

US 2016/0053031 A1 Feb. 25, 2016

Related U.S. Application Data

(63) Continuation of application No. 14/116,788, filed as application No. PCT/US2012/037462 on May 11, 2012, now Pat. No. 9,296,836.

(60) Provisional application No. 61/485,208, filed on May 12, 2011.

(51) Int. Cl.
| | |
|---|---|
| *C07F 11/00* | (2006.01) |
| *C08F 4/78* | (2006.01) |
| *C08F 10/00* | (2006.01) |
| *C08F 210/06* | (2006.01) |
| *C08F 110/06* | (2006.01) |
| *C08F 110/02* | (2006.01) |

(52) U.S. Cl.
CPC . *C08F 4/78* (2013.01); *C07F 11/00* (2013.01); *C08F 10/00* (2013.01); *C08F 110/02* (2013.01); *C08F 110/06* (2013.01); *C08F 210/06* (2013.01)

(58) Field of Classification Search
CPC ........ C07F 11/00; C07F 11/005; B01J 31/34; C08F 4/78; C08F 4/69112; C08F 4/69
See application file for complete search history.

(56) References Cited

U.S. PATENT DOCUMENTS

| | | | |
|---|---|---|---|
| 5,064,802 A | 11/1991 | Stevens et al. | |
| 5,153,157 A | 10/1992 | Hlatky et al. | |
| 5,296,433 A | 3/1994 | Siedle et al. | |
| 5,321,106 A | 6/1994 | LaPointe | |
| 5,350,723 A | 9/1994 | Neithamer et al. | |
| 5,425,872 A | 6/1995 | Devore et al. | |
| 5,470,993 A | 11/1995 | Devore et al. | |
| 5,625,087 A | 4/1997 | Devore et al. | |
| 5,707,913 A * | 1/1998 | Schlund ................. | C08F 10/00 |

(Continued)

FOREIGN PATENT DOCUMENTS

| | | | | |
|---|---|---|---|---|
| WO | 9400500 A1 | 1/1994 | | |
| WO | WO 99/19335 A1 * | 4/1999 | ............. | C07F 11/00 |
| WO | 0238628 A2 | 5/2002 | | |

OTHER PUBLICATIONS

Randall, A Review of High Resolution Liquid Carbon Nuclear Magnetic Resonance Characteristics of Ethylene-Based Polymers, Journal of Macromolecular Science, Part C: Polymer Reviews, vol. 29, No. 2, pp. 201-317, 1989.

(Continued)

*Primary Examiner* — Rip A Lee

(57) ABSTRACT

Provided is a non-cyclopentadienyl-based chromium-ligand complex, preferably a chromium-ligand complex of formula (J): $LCr(R^A)_m(D)_k$ (J), wherein L is a non-Cp monoanionic ligand; Cr (chromium) is in a formal oxidation state of +3 or +2; when Cr formally is $Cr^{+3}$, either m is 1 and $R^A$ is hydrocarbylene (a hydrocarbylene chromium-ligand complex of formula (J)) or m is 2 and each $R^A$ independently is hydrocarbyl (a dihydrocarbyl chromium-ligand complex of formula (J)), wherein each hydrocarbyl or hydrocarbylene of $R^A$ independently is unsubstituted or substituted by from 1 to 5 $R^{AS}$; each $R^{AS}$ independently is a neutral aprotic heteroalkyl, neutral aprotic heterocycloalkyl, neutral aprotic heteroaryl, or neutral aprotic aryl; when Cr formally is $Cr^{+2}$, m is 1 and $R^A$ is hydrocarbyl (a hydrocarbyl chromium-ligand complex of formula (J)); k is an integer of 0 or 1; D is absent when k is 0 or D is a neutral ligand when k is 1; wherein the chromium-ligand complex of formula (J) is overall neutral and lacks a cyclopentadienyl-based (Cp-based) moiety. Also provided is a chromium catalyst comprising or prepared from the complex. Also provided is a process of making the catalyst and a process employing the chromium catalyst for polymerizing the olefin monomer, especially a straight chain 1-alkene, to prepare the polyolefin, especially a partially chain-straightened poly(1-alkene) or olefin block copolymer. Further provided is the partially chain-straightened poly(1-alkene) or olefin block copolymer prepared thereby. Also provided is a high throughput workflow.

4 Claims, 2 Drawing Sheets

(56) References Cited

U.S. PATENT DOCUMENTS

| | | | | |
|---|---|---|---|---|
| 5,721,185 | A | 2/1998 | Lapointe et al. | 502/102 |
| 5,783,512 | A | 7/1998 | Jacobsen et al. | |
| 5,834,058 | A * | 11/1998 | Wallbridge | C07F 5/00 427/252 |
| 5,866,704 | A | 2/1999 | Nickias et al. | |
| 5,883,204 | A | 3/1999 | Spencer et al. | |
| 5,919,983 | A | 7/1999 | Rosen et al. | |
| 6,015,868 | A | 1/2000 | Nickias et al. | |
| 6,034,022 | A | 3/2000 | McAdon et al. | |
| 6,103,657 | A * | 8/2000 | Murray | C07F 7/00 502/155 |
| 6,150,297 | A | 11/2000 | Campbell et al. | |
| 6,242,623 | B1 * | 6/2001 | Boussie | C08F 10/00 502/104 |
| 6,268,444 | B1 | 7/2001 | Klosin et al. | |
| 6,303,714 | B1 * | 10/2001 | Kibino | C08F 10/00 502/104 |
| 6,320,005 | B1 | 11/2001 | Murray | |
| 6,515,155 | B1 | 2/2003 | Klosin et al. | |
| 6,555,634 | B1 | 4/2003 | Klosin et al. | |
| 6,696,379 | B1 | 2/2004 | Carnahan et al. | |
| 6,806,327 | B2 | 10/2004 | Campbell et al. | |
| 6,825,295 | B2 | 11/2004 | Klosin et al. | |
| 6,946,531 | B2 | 9/2005 | Graf et al. | |
| 6,953,764 | B2 | 10/2005 | Frazier et al. | |
| 7,091,292 | B2 | 8/2006 | Boussie et al. | |
| 7,098,356 | B2 | 8/2006 | Graf et al. | |
| 7,105,690 | B2 | 9/2006 | Schottek et al. | |
| 7,163,907 | B1 | 1/2007 | Canich et al. | |
| 7,202,373 | B2 | 4/2007 | Mihan | |
| 7,355,089 | B2 | 4/2008 | Chang et al. | |
| 7,435,701 | B2 | 10/2008 | Shen et al. | |
| 7,544,826 | B2 | 6/2009 | Mihan et al. | |
| 7,560,523 | B2 | 7/2009 | Coates et al. | |
| 7,608,668 | B2 | 10/2009 | Li Pi Shan et al. | |
| 7,629,464 | B2 | 12/2009 | Mihan et al. | |
| 7,858,706 | B2 | 12/2010 | Arriola et al. | |
| 7,897,679 | B2 | 3/2011 | Stevens et al. | |
| 7,947,787 | B2 | 5/2011 | Carnahan et al. | |
| 7,947,793 | B2 | 5/2011 | Marchand et al. | |
| 7,951,882 | B2 | 5/2011 | Arriola et al. | |
| 7,973,114 | B2 | 7/2011 | Mihan et al. | |
| 7,981,992 | B2 | 7/2011 | Arriola et al. | |
| 8,053,529 | B2 | 11/2011 | Carnahan et al. | |
| 8,076,147 | B2 | 12/2011 | Damme et al. | |
| 8,227,653 | B2 * | 7/2012 | Weber | C07C 2/30 526/75 |
| 8,318,874 | B2 | 11/2012 | Klosin et al. | |
| 8,476,393 | B2 | 7/2013 | Shan et al. | |
| 8,557,921 | B2 | 10/2013 | Arriola et al. | |
| 2005/0010039 | A1 | 1/2005 | Graf et al. | |
| 2008/0269445 | A1 | 10/2008 | Mihan | |
| 2015/0148502 | A1 * | 5/2015 | Christianson | C08F 10/00 526/131 |
| 2016/0053031 | A1 * | 2/2016 | Christianson | C08F 10/00 502/117 |

OTHER PUBLICATIONS

Kyle, Chemical and Process Thermodynamics, First Addition, pp. 206-317, Prentice-Hall, 1999.

Soave, Equilibrium Constants from a Modified Redlich-Kwong Equation of State, Chemical Engineering Science, pp. 1197-1203, 1972.

McAdams, et al., A Chromium Catalyst for the Polymerization of Ethylene as a Homogeneous Model for the Phillips Catalyst, Journal of the American Chemical Society, vol. 127, No. 4, pp. 1082-1083, 2005.

Champouret, et al., Homolytic Bond Strengths and Formation Rates in Half-Sandwich Chromium Alkyl Complexes: Relevance for Controlled Radical Polymerization, Angewandte Chemie, International Edition, vol. 47, No. 32, pp. 6069-6072, 2008.

* cited by examiner

NON-CYCLOPENTADIENYL-BASED CHROMIUM CATALYSTS FOR OLEFIN POLYMERIZATION

The present invention generally relates to a non-cyclopentadienyl-based chromium catalyst useful for polymerizing an olefin monomer, a non-cyclopentadienyl-based chromium precatalyst, a process for preparing a partially chain-straightened (PCS) polyolefin, a process for preparing an olefin block copolymer (OBC), and the PCS polyolefin and OBC prepared thereby; and a high throughput workflow.

Some olefin polymerization catalysts based on chromium or nickel are known, but only a few are recognized to be useful for partially chain-straightening polymerization of 1-alkenes. Also, no chromium catalysts have been used with a chain shuttling agent (CSA) and syndiotactic or isotactic olefin polymerization (SIOP) catalyst in an olefin polymerization process for making an OBC. For example, U.S. Pat. No. 7,544,826 B2 to Mihan S., et al. generically mention a certain monocyclopentadienyl-metal complex and a catalyst system comprising the monocyclopentadienyl-metal complex thereof, at least one activating compound C) together with a support component B), optionally one or more catalysts suitable for olefin polymerization as optional component D), and optionally a metal compound as additional component E), wherein the optional component E) is not identical to the component C). The metal of the monocyclopentadienyl-metal complex can be any one of more than 25 metals. Mihan S., et al. exemplify certain quinolinyl-substituted monocyclopentadienyl chromium dichloride complexes for polymerizing ethylene or a mixture of ethylene and hexene. However, Mihan et al. do not mention chain shuttling, a process for preparing an OBC, or OBC, and do not mention an embodiment of their catalyst system comprising a monocyclopentadienyl chromium complex and a SIOP catalyst. U.S. Pat. No. 7,560,523 B2 to Coates G. W. et al. generically mention certain chromium complexes and exemplify certain anthracenyl-based nickel catalysts for production of isotactic and regiorandom polypropylene based polymer and block copolymers. The complexes of Mihan et al. and Coates et al. are activated with a methylaluminoxane (MAO). Also, prior art chromium catalysts based on cyclopentadienyl, indenyl, and acenaphthenyl bidentate ligands inherently have limited structure diversification possibilities, and hence limited capability for tuning catalyst activity or selectivity by varying catalyst structure. None of the above prior art chromium catalysts have been used with a CSA and SIOP catalyst in a polymerization of an olefin to give an OBC. Also, Arriola D. J. et al. mention that well known chromium based heterogeneous catalysts can be used in the same process as a CSA and SIOP (WO 2006/101595 A1, page 19, lines 20-25). Heterogeneous catalysts by nature, however, cannot participate in chain shuttling with a requisite polymeryl-chain shuttling agent complex because the metal of the heterogeneous catalyst is not accessible thereto. This is because the metal is disposed inside pores of the solid support of the heterogeneous catalyst, and the polymeryl-chain shuttling agent complex is too large to diffuse into the pores.

Impact-modified poly(1-alkene)s (IMPA) have been prepared by sequentially polymerizing a 1-alkene with a SIOP catalyst to give a syndiotactic or isotactic poly(1-alkene) in a first reactor that contains only 1-alkene as olefin monomer, and transporting the syndiotactic or isotactic poly(1-alkene) into a second reactor that contains the 1-alkene and a desired percentage of ethylene relative to the 1-alkene in the second reactor, and copolymerizing the ethylene and 1-alkene in the second reactor with a same or different SIOP catalyst to give the impact-modified poly(1-alkene). The prior art process for preparing IMPAs has required two reactors.

A problem addressed by the present invention includes providing structurally diverse non-cyclopentadienyl-based chromium complexes and catalysts lacking a cyclopentadienyl-based moiety that can be used for catalyzing partial chain-straightening polymerization of a straight chain 1-alkene and unexpectedly for olefin polymerization for making an OBC.

BRIEF SUMMARY OF THE PRESENT INVENTION

The present invention provides a homogeneous non-cyclopentadienyl-based (non-Cp-based) chromium-ligand complex, wherein the chromium (Cr) is in a formal +3 or +2 oxidation state (see formula (J) below). The present invention also provides a process for preparing an OBC (see below), wherein the process employs a homogeneous non-Cp-based chromium catalyst, SIOP catalyst, CSA, and at least a 1-alkene. It would not have been predictable before the present invention that a homogeneous non-Cp-based chromium catalyst could or would participate in a polymeryl chain exchange reaction with a CSA. Surprisingly, the invention has discovered that the homogeneous non-Cp-based chromium catalyst is effective for participating in a polymeryl chain exchange reaction with the CSA, and thus is unexpectedly useful along with the SIOP catalyst in the process for preparing the OBC.

In a first embodiment the present invention provides a non-cyclopentadienyl-based chromium-ligand complex of formula (J): $LCr(R^A)_m(D)_k$ (J), wherein L is a non-Cp monoanionic ligand; Cr (chromium) is in a formal oxidation state of +3 or +2; when Cr formally is $Cr^{+3}$, either m is 1 and $R^A$ is hydrocarbylene (a hydrocarbylene chromium-ligand complex of formula (J)) or m is 2 and each $R^A$ independently is hydrocarbyl (a dihydrocarbyl chromium-ligand complex of formula (J)), wherein each hydrocarbyl or hydrocarbylene of $R^A$ independently is unsubstituted or substituted by from 1 to 5 $R^{AS}$; each $R^{AS}$ independently is a neutral aprotic heteroalkyl, neutral aprotic heterocycloalkyl, neutral aprotic heteroaryl, or neutral aprotic aryl; when Cr formally is $Cr^{+2}$, m is 1 and $R^A$ is hydrocarbyl (a hydrocarbyl chromium-ligand complex of formula (J)); k is an integer of 0 or 1; D is absent when k is 0 or D is a neutral ligand when k is 1; wherein the chromium-ligand complex of formula (J) is overall neutral and lacks a cyclopentadienyl-based (Cp-based) moiety. In formula (J), the L, $R^A$, $R^{AS}$, and D lack a Cp-based moiety.

In a second embodiment the present invention provides a chromium catalyst useful for polymerizing an olefin monomer, the chromium catalyst comprising a mixture or reaction product of the complex of formula (J) and an activating cocatalyst, wherein the ratio of total number of moles of the complex of formula (J) to total number of moles of the activating cocatalyst is from 1:10,000 to 100:1. Typically, the chromium catalyst is prepared (dissolved) in a suitable aprotic solvent (e.g., alkane(s), aromatic hydrocarbon(s), excess olefin monomer, or a mixture thereof). Preferably, the activating cocatalyst employed with the complex of formula (J) wherein Cr formally is $Cr^{+2}$ is an oxidizing cocatalyst that functions, at least in part, as an oxidant to convert in situ the formally $Cr^{+2}$ to the formally $Cr^{+3}$ complex or catalyst. The oxidizing cocatalyst can also be used as the activating cocatalyst with the formally $Cr^{+3}$ dihydrocarbyl and hydrocarbylene chromium-ligand complexes of formula (J). The activating cocatalyst and oxidizing cocatalyst subset thereof may be collectively referred to herein simply as the cocatalyst. Preferably, the cocatalyst is a boron-based cocatalyst. Other or additional cocatalysts can be used if desired.

In a third embodiment the present invention provides a process for polymerizing 1-alkene to prepare an olefin block copolymer, the process comprising contacting under olefin polymerizing conditions a first catalytically effective amount of a homogeneous non-cyclopentadienyl-based chromium catalyst with a chain shuttling agent (CSA), a second catalytically effective amount of a syndiotactic or isotactic olefin polymerization (SIOP) catalyst, and a straight chain 1-alkene having n carbon atoms to give an olefin block copolymer (OBC) comprising a partially chain-straightened (PCS) poly (1-alkene) atactic block and a syndiotactic or isotactic poly (1-alkene) block covalently bonded thereto, wherein the partially chain-straightened poly(1-alkene) block comprises a random distribution of poly(1-alkene) units and $(CH_2)_n$ units, both types of units being derived from the straight chain 1-alkene; and n is an integer of at least 3. The poly(1-alkene) units are 1,2-addition units and $(CH_2)_n$ units are 1,n-addition units. When n is 4 or higher in the 1-alkene (e.g., 1-butene, 1-pentene, or 1-hexene), in addition to 1,2- and 1,n-insertions to give, the 1-alkene wherein n is 4 or higher can insert 1,3- to 1,(n−1) to give from 1,3-addition units to 1,(n−1)-addition units, or a combination thereof. For example, 1-hexene can give 1,2- and 1,6-insertion as well as insertion that is 1,3-, 1,4-, 1,5-, or a combination thereof and the PCS poly(l-hexene) can comprise 1,2- and 1,6-addition units as well as addition unit(s) that is/are 1,3-, 1,4-, 1,5-, or a combination thereof. Also, PCS poly(1-butene) can further comprise 1,3-addition units in addition to its 1,2-addition units and $(CH_2)_4$ units. In some embodiments the process further employs ethylene as a comonomer and the atactic PCS poly(1-alkene) block comprises a PCS poly(ethylene-co-1-alkene) block comprising the $(CH_2)_n$ units and $(CH_2CH_2)_z$ units wherein z is an integer of at least 1. The z reflects the number of ethylene residuals incorporated in the PCS poly(ethylene-co-1-alkene) block. The number of $(CH_2)_n$ units in the PCS poly(1-alkene) block and PCS poly(ethylene-co-1-alkene) block independently is $[(CH_2)_n]_y$, wherein y is an integer of at least 1. The total number of $CH_2$ moieties in the PCS poly(1-alkene) block and PCS poly(ethylene-co-1-alkene) block independently equals y+2z. The chromium catalyst(s) employed in the process of the third embodiment always are homogeneous. At least one, preferably all employed chromium catalyst(s) lack a cyclopentadienyl-based ligand. Other than its lacking a cyclopentadienyl-based ligand, the homogeneous non-cyclopentadienyl-based chromium catalyst employed in this process, and the non-cyclopentadienyl-based chromium complex from which it is prepared, independently can contain any other ligand (e.g., halo, hydrogen, alkoxy, amino, or hydrocarbyl) other than a cyclopentadienyl-based ligand, which they lack. Preferably, the homogeneous non-cyclopentadienyl-based chromium catalyst is the chromium catalyst of the second embodiment. Preferably, the 1-alkene is propylene or 1-butene and the OBC comprises a PCS polypropylene or PCS poly(l-butene) atactic block and a syndiotactic or isotactic polypropylene or poly(l-butene) covalently bonded thereto. Preferably, the syndiotactic or isotactic polypropylene or poly(l-butene) block is an isotactic polypropylene (iPP) block or isotactic poly(1-butene) block.

The present invention also provides a process for polymerizing a 1-alkene to prepare a partially chain-straightened (PCS) polyolefin, the process comprising contacting under olefin polymerizing conditions a catalytically effective amount of the chromium catalyst of the second embodiment with a 1-alkene to give a PCS polyolefin. The PCS polyolefin comprises a random distribution of poly(1-alkene) units and $(CH_2)_n$ units, both types of units being derived from the straight chain 1-alkene; and n is an integer of at least 3. The poly(1-alkene) units are 1,2-addition units and $(CH_2)_n$ units are 1,n-addition units. In some embodiments the process further employs ethylene as a comonomer and the PCS poly(1-alkene) comprises a PCS poly(ethylene-co-1-alkene) comprising the $(CH_2)_n$ units and $(CH_2CH_2)_z$ units wherein z is an integer of at least 1. The z reflects the number of ethylene residuals incorporated in the PCS poly(ethylene-co-1-alkene). The number of $(CH_2)_n$ units in the PCS poly(1-alkene) and PCS poly(ethylene-co-1-alkene) independently is $[(CH_2)_n]_y$, wherein y is an integer of at least 1, preferably at least 2, and more preferably at least 3. The total number of $CH_2$ moieties from the $(CH_2CH_2)_z$ units and the 1,n-addition units in the PCS poly(1-alkene) and atactic segment of the PCS poly(ethylene-co-1-alkene) independently equals at least y+2z. The $(CH_2)_n$ units and $(CH_2CH_2)_z$ units can appear in the PCS poly(ethylene-co-1-alkene) contiguously, spaced apart by 1,2-addition units, or a combination thereof.

The present invention provides the PCS poly(1-alkene), or preferably the OBC from the third embodiment, wherein the PCS poly(1-alkene) is characterizable by a glass transition temperature $(T_g)$ at least 5° C. lower than $T_g$ of atactic polymer and exhibiting a peak in the $^{13}C$ nuclear magnetic resonance between 24 parts per million (ppm) and 30 ppm (e.g., near 24.8 ppm for PCS polypropylene and between 25 ppm and 30 ppm for PCS poly(1-butene)) and the OBC is characterizable by having a $T_g$ lower than the $T_g$ of a polyolefin prepared with the SIOP catalyst alone (SIOP polyolefin) and the OBC has a melting point $(T_m)$≤the $T_m$ of the SIOP polyolefin.

The present invention provides a manufactured article comprising the PCS poly(1-alkene) or OBC.

The present invention provides a process for preparing the complex of formula (J), the process comprising contacting a complex of formula (B): $LCr(Halo)_m(D)_k$ (B), or a tautomer thereof, with m mole equivalents of hydrocarbylMgHalo in a suitable aprotic solvent under preparation effective conditions to give a mixture comprising the complex of formula (J), or the tautomer thereof, aprotic solvent, and 1/m moles $Mg(Halo)_2$, wherein each Halo independently is Cl, Br, or I; and removing the solvent to give an isolated non-Cp-based chromium-ligand complex of formula (J), or the tautomer thereof, that is substantially free of haloaluminum. haloaluminum and L, m, D, and K are as defined for formula (J). When Cr is $Cr^{+2}$, m is 1; and when Cr is $Cr^{+3}$ m is 2. The complex of formula (J) prepared by this process typically is a solid. Preferably, the hydrocarbylMgHalo is an AlkylMgHalo.

The present invention also provides a process for selectively polymerizing ethylene (also known as ethene) in the presence of a 1-alkene, the process comprising a step of contacting together a catalytic amount of a homogeneous non-cyclopentadienyl-based chromium catalyst, ethylene, and a 1-alkene, wherein the contacting step is performed under olefin polymerizing conditions (described later) and prepares a rich polyethylene in contact with unpolymerized 1-alkene, the rich polyethylene being characterizable as having less than 5 mole percent (mol %) of a residual of the 1-alkene covalently incorporated therein as determined by nuclear magnetic resonance (NMR) spectroscopy (described later) and the olefin polymerizing conditions being characterizable by a reaction rate constant $k_{11}$ for adding the ethylene monomer to a reactive chain end comprising an ethylene residual; a reaction rate constant $k_{12}$ for adding the 1-alkene to a reactive chain end comprising the ethylene residual; and a reactivity ratio $r_1$ equal to $k_{11}$ divided by $k_{12}$ of greater than 10

(i.e., $r_1=k_{11}/k_{12}>10$). In some embodiments the process further employs a SIOP catalyst, and the chromium catalyst selectively polymerizes ethylene in the presence of the 1-alkene and the SIOP catalyst so as to give the rich polyethylene or a rich polyethylene segment of an OBC comprising the rich polyethylene segment covalently bonded to a syndiotactic or isotactic poly(1-alkene) segment. Other than its lacking a cyclopentadienyl-based ligand, the homogeneous non-cyclopentadienyl-based chromium catalyst employed in this process, and the non-cyclopentadienyl-based chromium complex from which it is prepared, independently can contain any other ligand (e.g., halo, hydrogen, alkoxy, amino, or hydrocarbyl) other than a cyclopentadienyl-based ligand, which they lack. Preferably, the homogeneous non-cyclopentadienyl-based chromium catalyst is the chromium catalyst of the second embodiment. The present invention also provides the polyethylene prepared by the invention process therefor.

The present invention also provides a process for preparing an impact-modified poly(1-alkene) (IMPA) in a single reactor, the process comprising a step of contacting together in a single reactor a first catalytically effective amount of a homogeneous non-cyclopentadienyl-based chromium catalyst, a second catalytically effective amount of a syndiotactic or isotactic olefin polymerization (SIOP) catalyst, and a 1-alkene, wherein the contacting step is performed under olefin polymerizing conditions (described later) and prepares the IMPA, the IMPA being characterizable as comprising a mixture of a syndiotactic or isotactic poly(1-alkene) polymer (sPA or iPA) and a partially-chain straightened (PCS) poly(1-alkene) polymer. In some embodiments this process further employs ethylene in the single reactor, and the process prepares an IMPA comprising a mixture of the syndiotactic or isotactic poly(1-alkene) polymer and a PCS poly(l-alkene-co-ethylene) copolymer. Preferably, the 1-alkene is propylene and the IMPA is an impact-modified polypropylene (IMPP). More preferably, the 1-alkene is propylene, the SIOP catalyst is an isotactic olefin polymerization (IOP) catalyst, and the IMPA is an impact-modified isotactic polypropylene (IMiPP). Other than its lacking a cyclopentadienyl-based ligand, the homogeneous non-cyclopentadienyl-based chromium catalyst employed in this process, and the non-cyclopentadienyl-based chromium complex from which it is prepared, independently can contain any other ligand (e.g., halo, hydrogen, alkoxy, amino, or hydrocarbyl) other than a cyclopentadienyl-based ligand, which they lack. Preferably, the homogeneous non-cyclopentadienyl-based chromium catalyst is the chromium catalyst of the second embodiment. In some embodiments the process further employs ethylene and prepares in the single reactor an ethylene/1-alkene block copolymer, which can be accomplished due to the selectivity of the homogenous non-cyclopentadienyl-based chromium catalyst for polymerizing ethylene.

The present invention also provides a high throughput workflow process for preparing a plurality of homogeneous non-cyclopentadienyl-based chromium complexes, catalysts prepared therefrom, partially chain straightened poly(1-alkene)s prepared therewith, or a combination thereof, the process comprising at least one of steps (a) to (c): (a) contacting under complex preparing conditions in each of a plurality of containers at least one penultimate chromium complex with a candidate monoanionic bidentate ligand, or the conjugate acid thereof, in an aprotic solvent in such a way so as to prepare a candidate homogeneous non-cyclopentadienyl-based chromium complex in the plurality of containers, wherein the penultimate chromium complex in each container is the same or, preferably, different, the candidate bidentate ligand in each container is the same or, preferably, different, and the prepared homogeneous non-cyclopentadienyl-based chromium complex in each container is the same or, preferably, different; (b) contacting under catalyst preparing conditions in each of the plurality of containers at least one activating cocatalyst with the candidate homogeneous non-cyclopentadienyl-based chromium complex in the aprotic solvent in such a way so as to prepare a candidate homogeneous non-cyclopentadienyl-based chromium catalyst in the plurality of containers, wherein the activating cocatalyst in each container is the same or, preferably, different, the candidate homogeneous non-cyclopentadienyl-based chromium complex in each container is the same or, preferably, different, and the prepared homogeneous non-cyclopentadienyl-based chromium catalyst in each container is the same or, preferably, different; and (c) contacting under olefin polymerizing conditions in each of a plurality of containers the candidate homogeneous non-cyclopentadienyl-based chromium catalysts and ethylene or a 1-alkene in such a way so as to prepare a polyethylene or partially chain straightened poly (1-alkene), respectively, in the plurality of containers, wherein the candidate homogeneous non-cyclopentadienyl-based chromium catalyst in each container is the same or, preferably, different, the 1-alkene in each container is the same or, preferably, different, and the polyethylene or prepared PCS poly(1-alkene) in each container is the same or, preferably, different. Preferred aprotic solvents are hydrocarbons (e.g., isoparaffinic alkanes or toluene). Preferably, the process comprises at least two and more preferably each of steps (a) to (c). Such high throughput workflow processes are especially useful as means for tuning chromium catalyst activity or selectivity by varying catalyst structure and composition, and for accelerating catalyst and polymerization research and development.

The present invention also provides the IMPA prepared by the invention process therefor, and preferably the IMPA is the IMPP, and more preferably the IMiPP.

The PCS poly(1-alkene), OBC, polyethylene, IMPA, and manufactured article are useful in a number of applications including, for example, elastic films for hygiene applications (e.g., for diaper covers); flexible molded goods for appliances, tools, consumer goods (e.g., toothbrush handles), sporting goods, building and construction components, automotive parts, and medical applications (e.g., medical devices); flexible gaskets and profiles for appliance (e.g., refrigerator door gaskets and profiles), building and construction, and automotive applications; adhesives for packaging (e.g., for use in manufacturing corrugated cardboard boxes), hygiene applications, tapes, and labels; and foams for sporting goods (e.g., foam mats), packaging, consumer goods, and automotive applications.

The present invention provides advantages. For example, the non-Cp-based chromium-ligand complex and chromium catalyst advantageously lack a cyclopentadienyl-based moiety, and preferably, dianiline, and therefore facilitates preparation of a wide variety of chromium catalyst structures. Thus, the chromium catalyst has capability for tuning catalyst activity (e.g., for a particular olefin monomer or under a particular set of olefin polymerization conditions) or selectivity (e.g., degree of chain straightening) by varying its structure. Also, unpredictably, the chromium-ligand complex and catalyst can be advantageously employed, and in some embodiments is employed, with the CSA and SIOP catalyst for polymerization of the 1-alkene (and, optionally, a comonomer as described later) for making the OBC. The OBC has a PCS poly(l-alkenyl) block (elastomeric, amorphous) and an isotactic (or syndiotactic) polyolefinyl block (non-elastomeric, crystalline character) covalently bonded thereto. Further, unexpectedly, the complex of formula (J) can be readily prepared, isolated, and preferably also purified to give the solid form thereof that is substantially free of haloaluminum. This is particularly valuable as the inventors discovered that haloaluminum species such as chloroaluminum species (e.g., chlorodialkylaluminum generated by contacting a chromium dichloride complex with a trialkylaluminum) poison SIOP catalysts in the olefin polymerization process to make the OBC, and consequently prevent formation of the OBC. This is because the complex of formula (A) requires activation with MAO or a trialkylaluminum, which activation naturally produces the undesirable haloaluminum species in situ. Since the molar ratio of Cr to metal of the SIOP catalyst is typically high (e.g., >1, in some embodiments from 2 to 20, and in other embodiments>20 (e.g., 50 or less)) in the invention process, the complex of formula (B) cannot be equally used, if at all, in place of the complex of formula (J) in the olefin polymerization process to make the OBC.

Additional embodiments and advantages are described in drawings and the remainder of the specification, including the claims.

BRIEF DESCRIPTION OF THE DRAWING(S)

Some embodiments of the present invention are described herein in relation to the accompanying drawing(s), which will at least assist in illustrating various features of the embodiments.

DETAILED DESCRIPTION OF THE PRESENT INVENTION

Figure 1:
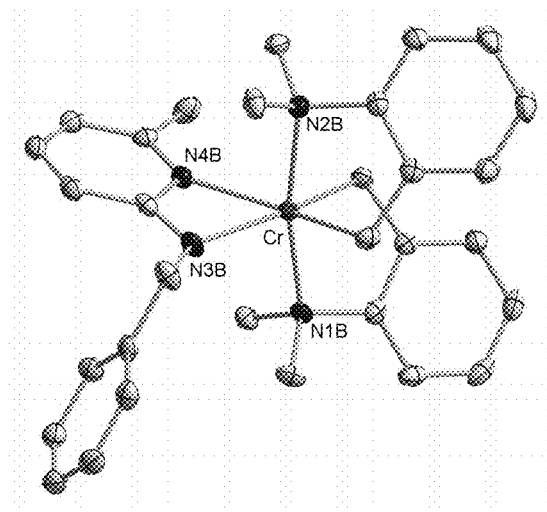
FIG. 1 shows an Oak Ridge Thermal Ellipsoid Plot (ORTEP) depiction of a single crystal structure derived by x-ray analysis of invention complex (1) (Example 1) with hydrogen atoms omitted for clarity.

The term "1-alkene" means an alpha-olefin, preferably a ($C_3$-$C_{40}$)alpha-olefin, and more preferably a straight chain ($C_3$-$C_{40}$)alpha-olefin. The term "candidate monoanionic bidentate ligand" means an organic compound comprising an anionic group and an aprotic heteroatom-containing functional group, which preferably is spaced-apart from the anionic indenyl group by at least two intervening carbon atoms. In some embodiments the organic compound contains, and preferably lacks a cyclopentadienyl-based moiety. The term "cyclopentadienyl" means a carbocyclic ring radical or preferably anion of formula $[C_5H_5]^-$ or $[C_5H_5]^-$, respectively, or a substituted analog thereof (e.g., a radical or anion of indene or fluorene, or of a substituted analog thereof (e.g., radical of chloroindene). The terms "syndiotactic or isotactic olefin polymerization catalyst" and "SIOP catalyst" are synonymous and mean a substance that does not contain chromium and that is effective for catalyzing polymerization of an olefin monomer to respectively give a syndiotactic or isotactic polyolefin as described later. In the process of the third embodiment, preferably the SIOP catalyst is the isotactic olefin polymerization (IOP) catalyst, and more preferably an IOP catalyst comprising a Group 4 metal which is titanium, still more preferably zirconium, or, even more preferably, hafnium. Also, preferably the syndiotactic or isotactic poly(1-alkene) block is the isotactic poly(1-alkene) block and the syndiotactic or isotactic poly(1-alkene) is the isotactic poly(1-alkene). As used herein the term "catalytically effective amount" means a quantity sufficient to facilitate catalysis (e.g., polymerization), wherein the quantity preferably is from 0.000001 mole percent (mol %) to 90 mol % of the product-limiting stoichiometric reactant employed. The term "olefin block copolymer" (OBC) means at least one molecule comprising at least two chemically distinct polyolefinyl segments wherein adjacent polyolefinyl segments are covalently bonded to each other and are preferably joined end-to-end in a linear manner. Preferably OBC means a composition that contains a sufficient amount of such molecules such that the composition may be properly classified as a block copolymer. The term "partially chain-straightened" means having at least some n,1-addition repeat units (i.e., $(CH_2)_n$ repeat units) wherein n is an integer≥3 and at least some 1,2-addition repeat units, wherein the n,1- and 1,2-addition repeat units are derived from a 1-alkene. The term "penultimate chromium complex" means a compound comprising a chromium(II) or (III) bonded to two or three, respectively, monoanionic leaving group ligands, which can be the same or different. In some embodiments each of the monoanionic leaving group ligands independently is an benzyl carbanion (e.g., 2-dimethylaminophenylmethyl carbanion), a phenyl carbanion (e.g., 4-methylphenyl carbanion), or halide. Preferably, each halide is chloride. The term "workflow" means an integrated process comprising steps of experimental design, mixing two or more materials together to give mixtures, independently analyzing the mixtures to determine one or more characteristics or properties thereof (e.g., degree of mixing), and collecting data from the resulting mixture analyses. In this context, the term "high throughput workflow" means the steps of the workflow are integrated and time-compressed such that an overall time to execute the integrated process of the high throughput workflow is from 2.0 times or more (e.g., 10, 50 or 100 times or more) faster than an overall time to execute a corresponding process of a standard non-high throughput workflow (e.g., any corresponding prior art process). Preferably, such processes employ a material dispensing robot for dispensing flowable materials, especially liquids, into the plurality of containers.

Numerical ranges: any lower limit of a range of numbers, or any preferred lower limit of the range, may be combined with any upper limit of the range, or any preferred upper limit of the range, to define a preferred aspect or embodiment of the range. Unless otherwise indicated, each range of numbers includes all numbers, both rational and irrational numbers, subsumed in that range (e.g., "from 1 to 5" includes, for example, 1, 1.5, 2, 2.75, 3, 3.81, 4, and 5).

Preferably, the isolated complex of formula (J) is purified (e.g., by trituration with a hydrocarbon solvent (e.g., benzene, toluene or hexanes) or recrystallization (e.g., from benzene, toluene, or hexanes) to give an isolated and purified complex of formula (J). In some embodiments the process of making the complex of formula (J), or the tautomer thereof, the mixture comprises solids disposed in a reaction liquor (liquid) and the method further comprises separating the solids (e.g., by filtration) from substantially all of the reaction liquor before the removing step to give the isolated complex of formula (J); triturating the isolated complex of formula (J) with a solvent (e.g., hydrocarbon solvent, e.g., toluene) to give an isolated and purified solid form of the complex of formula (J), or the tautomer thereof.

Preferably in the process for preparing the OBC, the homogeneous cyclopentadienyl-based chromium catalyst comprises the chromium catalyst of the second embodiment. Preferably, each $R^A$ independently is hydrocarbyl; more preferably aryl, unsubstituted alkyl, or alkyl substituted with a neutral aprotic aryl (aralkyl); and still more preferably unsubstituted aralkyl (e.g., benzyl) or unsubstituted alkyl. Preferably Cr is Cr formally is $Cr^{+3}$ and m is 2.

In the process of the third embodiment, preferably the SIOP catalyst is the isotactic olefin polymerization (IOP) catalyst, and more preferably an IOP catalyst comprising a Group 4 metal, which is titanium, zirconium, or, still more preferably, hafnium. Also, preferably the syndiotactic or isotactic poly(1-alkene) block is the isotactic poly(1-alkene) block. In some embodiments the process of making the complex of formula (J), or the tautomer thereof, further comprises filtering the mixture to remove solids therefrom before the removing step; triturating the solid complex of formula (J), or the tautomer thereof, with a hydrocarbon solvent to give a further isolated and purified solid non-Cp-based chromium-ligand complex of formula (J), or the tautomer thereof; or both.

In formula (J), in some embodiments m is 1, in others m is 2. In some embodiments k is 0, in others k is 1. Preferably, k is 0 such that D is absent. In some embodiments m is 2 and $R^A$ is alkyl. Preferably, $R^A$ is benzyl anion or 2-dimethylaminobenzyl anion. In formula (J), preferably the non-Cp monoanionic ligand (L) independently is a group that is hydrocarbyl, heterohydrocarbyl (preferably other than an aniline-based moiety), halide, nitrate, carbonate, phosphate, sulfate, $HC(O)O^-$, hydrocarbyl$C(O)O^-$, $HC(O)N(H)^-$, hydrocarbyl$C(O)N(H)^-$, hydrocarbyl$C(O)N$(hydrocarbyl)$^-$, $R^K R^L B^-$, $R^K R^L N^-$, $R^K O^-$, $R^K S^-$, $R^K R^L P^-$, or $R^M R^K R^L Si^-$, wherein each $R^K$, $R^L$, and $R^M$ independently is hydrogen, hydrocarbyl, or heterohydrocarbyl, or $R^K$ and $R^L$ are taken together to form a hydrocarbylene or heterohydrocarbylene and $R^M$ is as defined above, wherein each of the aforementioned groups lacks the Cp-based moiety. In addition to having an anionic functional group, optionally L further comprises a neutral functional group (e.g., pyridine-2-yl), which independently comprises at least one heteroatom that is O, N, S, or P. When L lacks the neutral functional group, L binds to Cr as a monodentate ligand. When L further comprises the neutral functional group, L typically binds to Cr as a monodentate ligand (e.g., when k is 1 and D is present in formula (J)) or, preferably, as a bidentate ligand (e.g., when k is 0 and D is absent). More preferably, the anionic functional group in L comprises the hydrocarbyl or an amidinyl, iminosulfonamido, triarylmethoxy, iminopyrrolyl, aminopyridinyl, or iminopyridinyl anion of the bidentate ligands L of any one of formulas (i) to (vi):

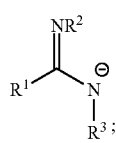
(i)

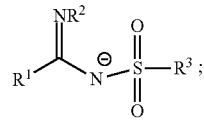
(ii)

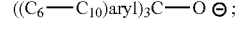
(iii)

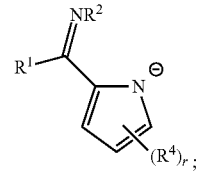
(iv)

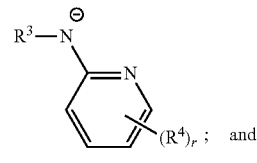
(v)

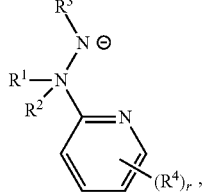
(vi)

respectively, or a tautomer thereof; wherein r is an integer of 0, 1, 2, or 3 in formula (v) and 0, 1, 2, 3, or 4 in formula (vi); each $R^1$, $R^2$, and $R^3$ independently is hydrogen (H), hydrocarbyl, or heterohydrocarbyl; each $R^4$ independently is H, halo, hydrocarbyl, or heterohydrocarbyl; or $R^3$ and one $R^4$ or any two adjacent $R^4$ independently can be taken together to form a hydrocarbylene or heterohydrocarbylene and the remainder of $R^4$, if any, is as defined previously; and the hydrocarbyl, heterohydrocarbyl, hydrocarbylene, and heterohydrocarbylene and $R^1$ to $R^4$ each lack a Cp-based moiety. When r is 0, $R^4$ is absent. In some embodiments the anionic functional group in L comprises the hydrocarbyl, in other embodiments the amidinyl anion of formula (i), in other embodiments the iminosulfonamido anion of formula (ii), in other embodiments the triarylmethoxy anion of formula (iii), in other embodiments the iminopyrrolyl anion of formula (iv), in other embodiments the aminopyridinyl anion of formula (v), and in other embodiments the iminopyridinyl anion of formula (vi). Preferably, each $R^1$ and $R^3$ independently is H or hydrocarbyl. Preferably, each $R^2$ independently is hydrocarbyl. Preferably, each halo independently is fluoro or chloro. Preferably, each aryl independently is a phenyl. Preferably each hydrocarbyl is alkyl (e.g., methyl, ethyl, or 1- or 2-propyl).

In formula (J) when D is present (i.e., k is 1), preferably the neutral ligand independently is a group that is a neutral Lewis base group that is $R^X NR^K R^L$, $R^K OR^L$, $R^K SR^L$, or $R^X PR^K R^L$, wherein each $R^X$ independently is H, hydrocarbyl, [hydrocarbyl]$_3$Si, [hydrocarbyl]$_3$Si-hydrocarbyl, or heterohydrocarbyl and each $R^K$ and $R^L$ independently is as defined above, wherein each of the aforementioned groups lacks the Cp-based moiety. Preferably, D is pyridine or a heterocycloalkyl (e.g., tetrahydrofuran, N-methylpyrrolidine, piperidine, or morpholine).

In some embodiments L in formula (J) is the conjugate base form of any one of the following compounds: N1-((1H-pyrrol-2-yl)methylene)-N2,N2-dimethylethane-1,2-diamine; diphenyl(pyridin-2-yl)methanol; N-(2-((benzylimino)methyl)phenyl)methanesulfonamide; N-((1H-pyrrol-2-yl)methylene)-2-methoxyethanamine; N-((1H-pyrrol-2-yl)methylene)-2-(methylthio)ethanamine; N-((1H-pyrrol-2-yl)methylene)-2-(benzylthio)ethanamine; N1-((1H-indol-2-yl)methylene)-N2,N2-dimethylethane-1,2-diamine; N-((1H-pyrrol-2-yl)methylene)-2-(diphenylphosphino)ethanamine; N-((1H-pyrrol-2-yl)methylene)-2-(di(propan-2-yl)phosphino)ethanamine; N-((1H-pyrrol-2-yl)methylene)-2-(pyrrolidin-1-yl)ethanamine; N-((1H-pyrrol-2-yl)methylene)-2-(piperidin-1-yl)ethanamine; N-methylisoquinolin-1-amine; 2,6-di(propan-2-yl)-N-((6-(naphthalen-1-yl)pyridin-2-yl)methylene)aniline; 4-chloro-N-((6-(4-chlorophenyl)pyridin-2-yl)methylene)-2,6-di(propan-2-yl)aniline; 3-((pyridin-2-ylmethyl)amino)butan-2-one oxime; 4-methyl-N-(2-(((4-methylphenyl)imino)methyl)phenyl)benzenesulfonamide; N-(2-((butylimino)methyl)phenyl)-4-methylbenzenesulfonamide; N-(2-((benzylimino)methyl)phenyl)-4-methylbenzenesulfonamide; N-(2-((benzylimino)methyl)phenyl)-2,4,6-tri(propan-2-yl)benzenesulfonamide; 9-(4-methoxypyrimidin-5-yl)-9H-xanthen-9-ol; bis(4-methoxypyrimidin-5-yl)(phenyl)methanol; bis(4-ethoxypyrimidin-5-yl)(phenyl)methanol; 1-(2-ethoxy-6-methoxyphenyl)-2-methyl-1-phenylpropan-1-ol; N-([1,1'-biphenyl]-2-yl(6-naphthalen-1-yl)pyridin-2-yl)methyl-2,6-di(propan-2-yl)aniline; N-benzyl-6-methylpyridin-2-amine; $N^1$-(isoquinolin-1-yl)-$N^2,N^2$-dimethylethane-1,2-diamine; N-(2-methoxyethyl)isoquinolin-1-amine; $N^1$-(isoquinolin-1-yl)-$N^3,N^3$-dimethylpropane-1,3-diamine; N-((tetrahydrofuran-2-yl)methyl)isoquinolin-1-amine; $N^1$-(isoquinolin-1-yl)-$N^3,N^3$,2,2-tetramethylpropane-1,3-diamine; 2,3-dihydro-1H-pyrrolo[2,3-b]pyridine; N-(furan-2-ylmethyl)isoquinolin-1-amine; 1,2-dihydropyrrolo[4,3,2-ij]isoquinoline; 2,3-dihydro-1H-benzo[de][1,8]naphthyridine; and N,N'-Diphenylbenzamidine.

In some embodiments the non-cyclopentadienyl-based chromium-ligand complex of formula (J) is the complex of any one of complexes (1) to (7):

(1)

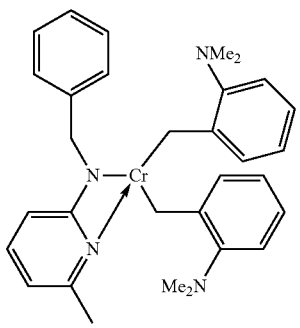

(2)

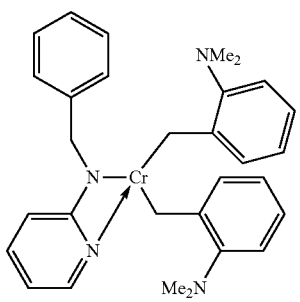

(3)

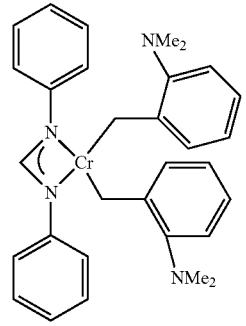

(4)

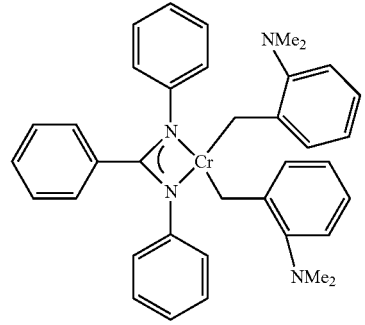

(5)

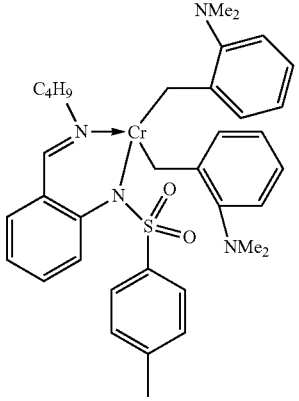

(6)

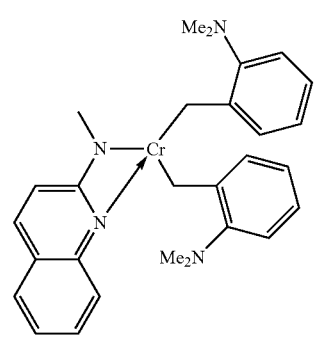

(7)

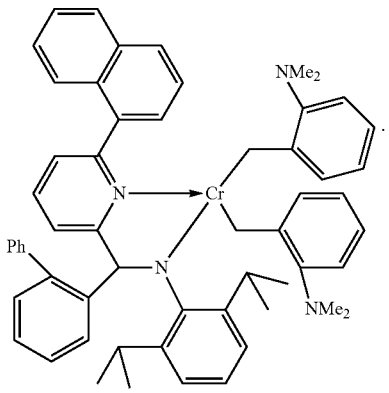

In the OBC the inserted $(CH_2)_n$ units are derived from alpha,omega reactivity of the straight chain 1-alkene. A preferred straight chain 1-alkene is propene (i.e., propylene), wherein n is 3, or 1-butene, wherein n is 4. In another embodiment the present invention provides the PCS poly(1-alkene), wherein the PCS poly(1-alkene) is characterizable by analogously to the characterization of the PCS poly(1-alkene) block (or segment) of the OBC described later. Preferably, the PCS poly(1-alkene) is characterizable as having a $T_g$ at least 5° C. lower than $T_g$ of tactic polymer and exhibiting a peak (signal) in the $^{13}C$ nuclear magnetic resonance near 24.8 parts per million. In another embodiment the present invention provides a manufactured article comprising the PCS poly(1-alkene), or a combination of the OBC of the fourth embodiment and the PCS poly(1-alkene). The PCS poly(1-alkene), combination, and ad rem manufactured articles are also useful in the aforementioned applications.

The present invention provides a number of additional advantages. For example, the chromium catalyst is valuable because it can catalyze partial chain-straightening polymerization of a straight chain 1-alkene. This preferred polymerization gives some straight chain 1-alkene molecules in a 1,2-addition fashion and others in a n,1-addition fashion, wherein n is the number of carbon atoms of the straight chain 1-alkene (e.g., n is 3 for propylene). As a result, the PCS poly(1-alkene) typically has fewer branches and a lower glass transition temperature ($T_g$) than a corresponding syndiotactic or isotactic poly(1-alkene), which substantially lacks n,1-addition repeat units. The PCS poly(1-alkene) is characterizable as being atactic and regio-irregular and as having advantageous elastomeric properties (e.g., low Young's modulus or high yield strain compared with a corresponding isotactic poly(1-alkene)). Thus by varying the chromium catalyst's structure, it is expected that PCS poly(1-alkenes) with varying degrees of 1,2-addition and n, 1-addition and varying degrees of elastomeric properties can be prepared by different embodiments of the invention process. In some aspects the PCS poly(1-alkenes) would have novel structure and properties that enable improved or new polyolefin applications in addition to those recited previously.

The term "hydrocarbylene" means a hydrocarbon diradical having at least one carbon atom wherein each hydrocarbon diradical independently is aromatic or non-aromatic; saturated or unsaturated; straight chain or branched chain; cyclic or acyclic; unsubstituted or substituted; or a combination of at least two thereof. The radicals of the hydrocarbon diradical can be on same or, preferably, different carbon atoms. The term "alkylene" is a hydrocarbylene wherein the hydrocarbon diradical is non-aromatic, saturated, straight chain or branched, acyclic, and unsubstituted or substituted. The term "hydrocarbyl" is as defined previously for hydrocarbylene except whereas hydrocarbylene is the diradical, the hydrocarbyl is a monoradical and so has a hydrogen atom in place of the second radical of the diradical. Preferably, the hydrocarbyl and hydrocarbylene lack a cyclopentadienyl-based moiety. The term "alkyl" is a hydrocarbyl wherein the hydrocarbon radical is non-aromatic, saturated, straight chain or branched, acyclic, and unsubstituted or substituted. Preferably, the substituent of the substituted alkyl is aryl. The term "heterohydrocarbylene" means a heterohydrocarbon diradical having at least one carbon atom and from 1 to 6 heteroatoms; wherein each heterohydrocarbon diradical independently is aromatic or non-aromatic; saturated or unsaturated; straight chain or branched chain; cyclic or acyclic; unsubstituted or substituted; or a combination of at least two thereof. The radicals of the heterohydrocarbon diradical can be on same or, preferably, different atoms, each radical-bearing atom independently being carbon or heteroatom. The term "heterohydrocarbyl" is as defined previously for heterohydrocarbylene except whereas heterohydrocarbylene is the diradical, the heterohydrocarbyl is a monoradical. The term "heteroalkyl" is a heterohydrocarbyl that is a radical of a saturated, straight or branched heterohydrocarbon having at least one carbon atom. The term "heterocycloalkyl" is a heterohydrocarbyl that is a radical of a saturated, cyclic heterohydrocarbon having at least one carbon atom. The term "heteroaryl" is a heterohydrocarbyl that is a radical of an aromatic cyclic heterohydrocarbon having at least 5 ring atoms, wherein at least one of the 5 ring atoms is a carbon atom. The term "aryl" is a hydrocarbyl that is a radical of an aromatic cyclic hydrocarbon having at least 6 carbon atoms. The term "neutral aprotic" when used to modify the heteroalkyl, heterocycloalkyl, heteroaryl, or aryl means the heteroalkyl, heterocycloalkyl, heteroaryl, and aryl lack a heteroatom-hydrogen moiety (e.g., lack an O—H, N—H, S—H, or P—H moiety, or any moiety having a pKa<35, or lack all of the foregoing heteroatom-hydrogen moieties). Examples of neutral aprotic heteroalkyl are $CH_3O$—; $CH_3(CH_2)_{24}O$—; $CH_3O(CH_2)_2$—; $CH_3S$—; $CH_3S(CH_2)_2$—; $CH_3S(O)$—; $CH_3S(O)_2$—; $(CH_3CH_2)_2N$—; $(CH_3CH_2)_2N(CH_2)_2$—; and $(CH_3CH_2)_2NS(O)_2$—. Examples of neutral aprotic heterocycloalkyl are tetrahydrofuran-2-yl; tetrahydropyrane-2-yl; pyrrolidin-1-yl; morpholin-4-yl; piperidine-1-yl; and 4-methylpiperazin-1-yl. Examples of neutral aprotic heteroaryl are tetrazol-1-yl; furan-2-yl; pyrrol-1-yl; imidazol-1-yl; pyridin-2-yl; pyridin-3-yl; pyrimidin-2-yl; indol-1-yl; 1,2-benzisoxazol-3-yl; 1,2-benzisoxazol-7-yl; quinolin-2-yl; isoquinolin-1-yl; and carbozol-9-yl. Examples of neutral aprotic aryl are phenyl and naphthyl.

Other than $R^A$, each hydrocarbyl, heterohydrocarbyl, hydrocarbylene, heterohydrocarbylene, alkylene, and heteroalkylene group independently is unsubstituted or substituted with one or more substituents $R^S$ (up to and including persubstitution by $R^S$); and each $R^S$ independently is selected from the group consisting of a halogen atom (halo); any one of polyfluoro and perfluoro substitution; unsubstituted alkyl; $F_3C$—; $FCH_2O$—; $F_2HCO$—; $F_3CO$—; $R^V{}_3Si$—; $R^GO$—; $R^GS$—; $R^GS(O)$—; $R^GS(O)_2$—; $R^G{}_2P$—; $R^G{}_2N$—; $R^G{}_2C=N$—; NC—; oxo (i.e., =O); imino (=$NR^G$); $R^GC(O)O$—; $R^GOC(O)$—; $R^GC(O)N(R^G)$—; and $R^G{}_2NC(O)$—, wherein each $R^G$ independently is a hydrogen atom or an unsubstituted alkyl and each $R^V$ independently is a hydrogen atom, an unsubstituted alkyl, or an unsubstituted alkoxy. In some embodiments there is at most 3 $R^S$, in other embodiments at most 2 $R^S$, and in other embodiments at most 1 $R^S$. In some embodiments there are 3 $R^S$, in other embodiments 2

$R^S$, in other embodiments 1 $R^S$, and in other embodiments 0 $R^S$. In some embodiments $R^S$ independently is halo; in other embodiments unsubstituted alkyl; in other embodiments polyfluoro or perfluoro substitution; in other embodiments $F_3C$—; $FCH_2O$—; $F_2HCO$—; or $F_3CO$—; in other embodiments $R^V_3Si$—; in other embodiments $R^GO$—; in other embodiments $R^GS$—; $R^GS(O)$—; or $R^GS(O)_2$—; in other embodiments $R^G_2P$—; in other embodiments $R^G_2N$—; and in other embodiments $R^G_2C$=N—; NC—; oxo (i.e., =O); imino (=$NR^G$); $R^GC(O)O$—; $R^GOC(O)$—; $R^GC(O)N(R^G)$—; or $R^G_2NC(O)$—. Preferably, each $R^S$ independently is the $R^{AS}$.

In some embodiments the present invention contemplates unsubstituted chemical groups or molecules described herein have an upper limit of at most 40 carbon atoms, but the invention includes other embodiments having upper limits of lower or higher numbers of carbon atoms (e.g., at most any one of 4, 6, 8, 10, 12, 15, 20, 30, 39, 60, 100, 1,000, and 100,000 carbons). Likewise in some embodiments the present invention contemplates such unsubstituted chemical groups or molecules have a lower limit of at least 1 carbon atom, but the invention includes embodiments having higher lower limits (e.g., at least any one of 2, 3, 4, 5, 6, 7, and 8 carbons), especially higher lower limits as would be well known for a smallest aspect of the chemical group or molecule (e.g., at least 3 carbons for a cycloalkyl or alpha-olefin).

The term "halo" means fluoro, chloro, bromo, or iodo; or in an increasingly preferred embodiment chloro, bromo or iodo; chloro or bromo; or chloro. The term "heteroatom" means O, S, S(O), S(O)$_2$, N($R^N$), Si($R^C$)$_3$, Ge($R^C$)$_3$, or P($R^P$); or preferably O, S, S(O), S(O)$_2$, N($R^N$); wherein each $R^C$, $R^P$, and $R^N$ independently is unsubstituted (C$_1$-C$_{18}$)hydrocarbyl or $R^N$ absent (when N comprises —N=).

The present invention also provides another process for preparing the chromium-ligand complex of formula (J) or the chromium catalyst. In a first method, the chromium-ligand complex of formula (J) or the chromium catalyst is prepared by a comproportionation reaction comprising contacting a chromium(II) compound of formula Cr(L)$_2$ (i.e., Cr formally is Cr$^{+2}$) with a chromium(IV) compound of formula Cr(R$^A$)$_4$. In a second method, the chromium-ligand complex of formula (J) or the chromium catalyst is prepared by a deprotonation reaction comprising contacting a chromium(III) compound of formula Cr(R$^A$)$_3$ (i.e., Cr formally is Cr$^{+3}$) with a compound of formula L-H, wherein L-H is the conjugate acid form of L. When $R^A$ is alkyl, the comproportionation and deprotonation reactions can prepare the chromium catalyst directly. In a third method, the chromium-ligand complex of formula (J) is prepared by a displacement reaction comprising contacting a chromium(III) compound of formula Cr(R$^A$)$_3$ with L or L-H, and then, if desired, contacting the resulting complex sequentially with the alkylating agent and then the cocatalyst to prepare the chromium catalyst. In a fourth method, the chromium-ligand complex of formula (J) is prepared by an oxidation reaction comprising contacting a chromium(II) compound of formula LCrR$^A$ with an oxidant (e.g., oxidant is a borate or dimethylene chloride) and then, if desired, contacting the resulting complex the cocatalyst to prepare the chromium catalyst. Preferably, the chromium-ligand complex is isolated from a reaction mixture of the methods before being contacted with the alkylating agent or cocatalyst. Each of the contacting steps independently is performed under preparation effective conditions described later. In these reactions, a neutral ligand D optionally can be added (e.g., before the cocatalyst) or omitted (k is 0). Preparation of the complex of formula (J) according to the invention process can be fully illustrated by preparation of a complex of formula (J1) wherein m is 2, each R$^A$ is hydrocarbyl, and Cr formally is Cr$^{+3}$ as illustrated below in Scheme 1:

(J1)

Alternatively, preparation of the complex of formula (J) according to the invention process can be fully illustrated by preparation of a complex of formula (J2) wherein m is 1, R$^A$ is hydrocarbyl, and Cr formally is Cr$^{+2}$ as illustrated below in Scheme 2:

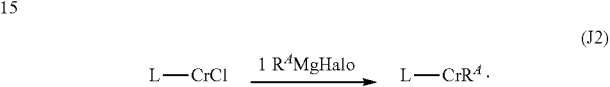
(J2)

Alternatively, the invention provides a process for preparing the complex of formula (J) that is a complex of formula (J3) wherein m is 1, R$^A$ is an unsubstituted hydrocarbylene derived from an unsubstituted alpha,omega-diene having at least q carbon atoms wherein q is an integer of 4 or more, and Cr formally is Cr$^{+3}$ as illustrated below in Scheme 3:

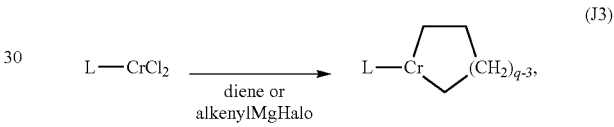
(J3)

wherein the C=C and MgHalo of the alkenylMgHalo are and different terminus of the alkenylMgHalo.

The monoanionic non-Cp ligand L preferably is prepared directly by deprotonation of an acidic proton of its conjugate acid form. Examples of the conjugate acid form are secondary amines having an N—H acidic proton, including cyclic secondary amines such as pyrrolidines; alcohols having an O—H acidic proton; thiols having an S—H acidic proton, and phosphines having a P—H acidic proton. Alternatively, such L can be prepared indirectly by a condensation reaction of a penultimate compound having an electrophilic functional group with an anionic nucleophilic group (e.g., a carbanion), which reacts with and covalently bonds to the electrophilic functional group in such a way so as to form an anionic product the anion and aprotic neutral heteroatom-containing functional group. Examples of suitable electrophilic functional groups are aldehydes (e.g., benzaldehydes) ketones (e.g., acetophenones), imines (e.g., alkylamine derivatives of acetophenones), and carbodiimides (e.g., N,N-dimethyl-2-(2-(((phenylimino)methylene)amino)benzyl)aniline) The bidentate monoanionic ligand (not shown) can then be contacted with the Cr(halo)$_2$(THF)$_p$, wherein preferably p is an integer of 1, 2 or 3 or Cr(halo)$_3$(THF)$_3$, as the case may be, to give a corresponding chromium dichloride complex, which can be converted to complex of formula (J) by contacting the dichloride complex with a Grignard reagent of formula RMgHalo, wherein Halo is fluoro, iodo, bromo, or preferably chloro. An example employing the N,N-dimethyl-2-(2-(((phenylimino) methylene)amino)benzyl)aniline (c1) as the penultimate compound and a carbanion from an organolithium RLi as the anionic nucleophilic group gives, after contacting with Cr(halo)$_3$(THF)$_3$, a corresponding chromium dichloride complex of formula (C) is shown in Scheme 3:

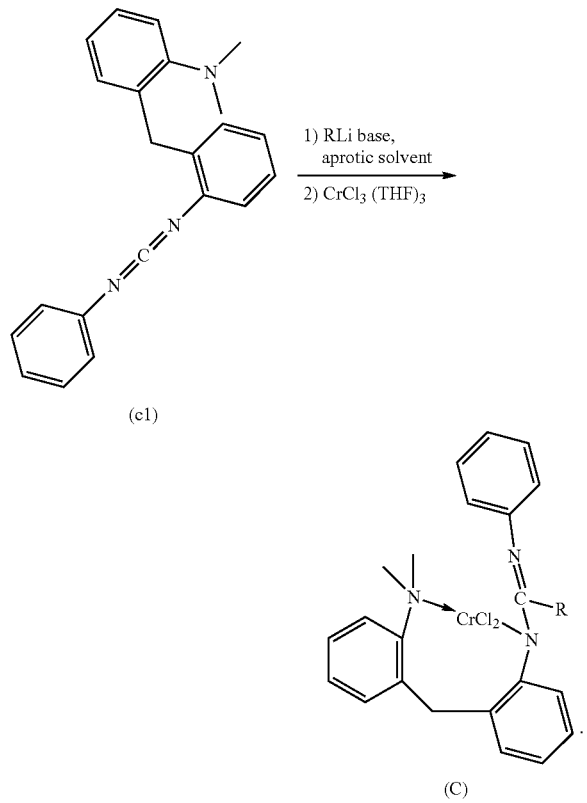

(c1)

(C)

In the 1-alkene polymerization, if desired the CSA can be used to prolong lifetime of, i.e., safekeep, a PCS poly(1-alkene) polymeryl chain such that a substantial fraction of the polymeryl chains exit at least a first reactor of a multiple reactor series or a first reactor zone in a multiple zoned reactor operating substantially under plug flow conditions in the form of a radical (polymeryl), and the polymeryl chains experience different polymerization conditions in the next reactor or polymerization zone. The term "chain shuttling agent" generally refers to a compound or mixture of such compounds that is capable of causing polymeryl (i.e., polymer chain) exchange between at least two active catalyst sites of a same olefin polymerization catalyst or between at least two active catalyst sites of at least two different olefin polymerization catalysts under the olefin polymerization conditions. That is, transfer of a polymer fragment occurs both to and from one or more of active sites of the olefin polymerization catalysts. Examples of the CSA are aluminum-based CSAs (e.g., tri(n-octyl)aluminum) and zinc-based CSAs (e.g., diethyl zinc) as described in US 2008/0269412 A1. Zinc-based CSAs are preferred, dialkyl zinc CSAs are more preferred, and diethyl zinc still more preferred. In contrast to a chain shuttling agent, a "chain transfer agent" causes termination of polymer chain growth and amounts to a one-time transfer of polymer from a catalyst to the chain transfer agent.

The PCS poly(1-alkene) elastomeric segment of the OBC typically has a $T_g<15°$ C. and is called herein a "soft segment." The syndiotactic or isotactic poly(1-alkene) segment of the OBC typically has a $T_g>50°$ C. or melting temperature $(T_m)>50°$ C. and is called herein a "hard segment." The $T_g$ and $T_m$ are determined by differential scanning calorimetry (DSC) as described later. In some embodiments the hard segment comprises a polyethylene or isotactic polypropylene. The terms "isotactic polyolefin" and "syndiotactic polyolefin" mean a polymeryl molecule having at least 70% of pentads having a head-to-tail (1,2-addition) arrangement of olefin monomer repeat units having a stereoregularity of same or alternating, respectively, chiral centers as determined by $^{13}$C-NMR spectroscopy.

Preferably the $T_g$ of the OBC is at least 5° C. lower, more preferably at least 10° C. lower, and still more preferably at least 30° C. lower than the $T_g$ of the SIOP polyolefin. Preferably, the $T_m$ of the OBC>$T_g$ of the SIOP polyolefin. The molecular weight distribution, as determined by GPC, of the OBC preferably is narrower than a blend of PCS and SIOP polyolefins. Preferably, $^{13}$C NMR on the OBC reveals both the presence of at least three contiguous methylene units as well as signals attributable to tactic polyolefin (syndiotactic or isotactic polyolefin). To distinguish between the OBC and the blend, a crystallization analysis fraction (CRYSTAF) or temperature-rising elution fractionation (TREF) elution curve should reveal >2%, more preferably >10%, still more preferably >50% fraction that elutes in-between the SIOP polyolefin and the OBC. Analysis of this in-between-eluting fraction by $^{13}$C NMR preferably reveals the presence of both the OBC and SIOP polymer. The OBC can also be characterized by ad rem methods of US 2010/0093964 A1. Preferably, the OBC is characterizable such that any branches in the PCS poly(1-alkene) block (or segment) are the same length as or shorter than the branches in the SIOP polymer. In addition, the number of contiguous methylene units in the PCS poly(1-alkene) block (or the PCS poly(1-alkene) can be increased by the aforementioned addition of ethylene as a co-monomer, preferably while not substantially lowering the $T_m$ of the SIOP polyolefin, and more preferably while not lowering the $T_m$ of the SIOP polyolefin at all. Even so, OBC having $T_m$ up to 75° C. lower than the SIOP polyolefin can still make useful OBCs. In addition, the distribution of segment lengths within the OBC can be described as a most-probable distribution, which is more broad than that obtained by using living catalysts to make non-invention OBCs, and without the need to blend in a second (or third, etc.) polyolefin. Preferably, the molecular weight distribution of the OBC will also be most-probable, preferably 2.0 or greater as determined by GPC, without the need to blend the OBC polymer with a second (or third, etc.) polymer, which molecular weight distribution is also unlike OBCs made by living catalysts, which have molecular weight distributions generally less than 2.0 as determined by GPC analysis.

The SIOP catalyst can be prepared by contacting a SIOP-suitable metal-ligand complex with a suitable cocatalyst, preferably an aluminum-based cocatalyst as described later. The metal of the metal-ligand complex and SIOP catalyst can be a metal of any one of Groups 3 to 15, and preferably Group 4, of the Periodic Table of the Elements. In some embodiments the Group 4 metal is titanium, in other embodiments zirconium, and more preferably hafnium. Examples of types of SIOP-suitable metal-ligand complexes are metallocene, half-metallocene, constrained geometry, and polyvalent pyridylamine-, polyether-, or other polychelating base complexes. Such metal-ligand complexes are described in US 2010/0069573 A1. Other SIOP-suitable metal-ligand complexes are those described in U.S. Pat. No. 5,064,802; U.S. Pat. No. 5,153,157; U.S. Pat. No. 5,296,433; U.S. Pat. No. 5,321,106; U.S. Pat. No. 5,350,723; U.S. Pat. No. 5,425,872; U.S. Pat. No. 5,470,993; U.S. Pat. No. 5,625,087; U.S. Pat. No. 5,721,185; U.S. Pat. No. 5,783,512; U.S. Pat. No. 5,866,704; U.S. Pat. No. 5,883,204; U.S. Pat. No. 5,919,983; U.S. Pat. No. 6,015,868; U.S. Pat. No. 6,034,022; U.S. Pat. No. 6,103,657; U.S. Pat. No. 6,150,297; U.S. Pat. No. 6,268,444; U.S. Pat. No. 6,320,005; U.S. Pat. No. 6,515,155; U.S. Pat.

No. 6,555,634; U.S. Pat. No. 6,696,379; U.S. Pat. No. 7,163, 907; and U.S. Pat. No. 7,355,089, as well as in applications WO 02/02577; WO 02/92610; WO 02/38628; WO 03/40195; WO 03/78480; WO 03/78483; WO 2009/012215 A2; US 2003/0004286; US 2004/0220050; US 2006/0199930 A1; US 2007/0167578 A1; US 2008/0275189 A1; and US 2008/0311812 A1. More preferred are the SIOP catalysts described in US 2007/0167578 A1, paragraphs numbered [0138] to [0476]. Still more preferred is Example 1 of US 2004/0220050 A1 of formula (SIOP-1):

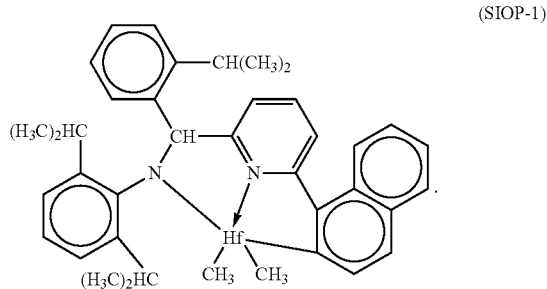

(SIOP-1)

Also preferred is the dibenzyl hafnium complex (SIOP-2a) prepared with ligand LL121 and tetrabenzylhafnium as in Examples 19.8 and 19.9 of US 2006/0025548 A1 and the analogous dimethyl hafnium complex (SIOP-2b) prepared with ligand LL121 and tetramethylhafnium using a procedure analogous to that of Examples 19.8 and 19.9 of US 2006/0025548 A1.

The chromium catalyst and SIOP catalyst independently can be prepared by a number of different methods that generally involve independently contacting the complex of formula (J) or the SIOP-suitable metal-ligand complex, or a combination thereof, with a suitable cocatalyst under preparation effective conditions. The preparation methods are not critical and various methods are effective. Many suitable cocatalysts, alkylating agents, and activating techniques have been previously taught with respect to different metal-ligand complexes in the following USPNs: U.S. Pat. No. 5,064,802; U.S. Pat. No. 5,153,157; U.S. Pat. No. 5,296,433; U.S. Pat. No. 5,321,106; U.S. Pat. No. 5,350,723; U.S. Pat. No. 5,425, 872; U.S. Pat. No. 5,625,087; U.S. Pat. No. 5,721,185; U.S. Pat. No. 5,783,512; U.S. Pat. No. 5,883,204; U.S. Pat. No. 5,919,983; U.S. Pat. No. 6,696,379; and U.S. Pat. No. 7,163, 907. Combinations of one or more of the alkylating agents, one or more of the cocatalysts, optionally, one or more of the activating techniques, or variants thereof are also contemplated. A suitable activating technique is bulk electrolysis.

Preferred cocatalysts for the complex of formula (J) are boron-based. Preferred boron-based cocatalysts are tri(($C_6$-$C_{18}$)aryl)boron compounds and halogenated (including perhalogenated) derivatives thereof, (e.g., tris(pentafluorophenyl)borate, trityl tetrafluoroborate (TTB), trityl tetrakis (pentafluorophenyl)borate; ferrocenium tetrakis (pentafluorophenyl)borate; or, more preferably a trialkylammonium or tris(4-halo)aminium tetrakis(pentafluorophenyl)borate such as bis(octadecyl)methylammonium tetrakis(pentafluorophenyl)borate ([HNMe($C_{18}H_{37}$)$_2$][B($C_6F_5$)$_4$], abbreviated as BOMATPB)) or tris(4-bromo) aminium tetrakis(pentafluorophenyl)borate ([(4-BrPh)$_3$N][B($C_6F_5$)$_4$]). The term "ferrocenium" means a biscyclopentadienyl iron(III) radical cation of formula [($C_5H_5$)$_2$Fe]$^+$. Preferred aluminum-based alkylating agents and cocatalysts independently include alkyl aluminums; polymeric or oligomeric alumoxanes (also known as aluminoxanes); neutral Lewis acids; and non-polymeric, non-coordinating, ion-forming compounds (including the use of such compounds under oxidizing conditions). The term "alkyl aluminum" means a monoalkyl aluminum dihydride or monoalkylaluminum dihalide, a dialkyl aluminum hydride or dialkyl aluminum halide, or a trialkylaluminum. Preferably the alkyl of the foregoing alkyl-aluminums is from 1 to 10 carbon atoms. Triethylaluminum is more preferred. Aluminoxanes and their preparations are known at, for example, U.S. Pat. No. 6,103,657. Examples of preferred polymeric or oligomeric alumoxanes are methylalumoxane, triisobutylaluminum-modified methylalumoxane (MMAO), and isobutylalumoxane. In some embodiments at least two of the cocatalysts are used in combination with each other. In some embodiments the cocatalyst comprises FTPFPB, in other embodiments BOMATPB, in other embodiments MMAO, in other embodiments FTPFPB and MMAO, and in other embodiments BOMATPB and MMAO.

The ratio of total number of moles of any metal-ligand complex (e.g., chromium-ligand complex of formula (J) and the syndiotactic and isotactic metal-ligand complexes) to total number of moles of one or more of the cocatalysts preferably independently is at least 1:5000, more preferably at least 1:1000; and 10:1 or less, more preferably 1:1 or less. When tris(pentafluorophenyl)borane alone is used as the cocatalyst, preferably the number of moles of the tris(pentafluorophenyl)borane that are employed to the total number of moles of one or more olefin polymerization catalysts form 0.5:1 to 10:1, more preferably from 1:1 to 6:1, still more preferably from 1:1 to 5:1. The remaining cocatalysts are generally employed in approximately mole quantities equal to the total mole quantities of one or more olefin polymerization catalysts. The syndiotactic and isotactic olefin polymerization catalysts can be prepared under the preparation effective conditions.

Increasing the molar ratio of TTB to cyclopentadienyl-based chromium-ligand complex (e.g., the complex of formula (J)) from 1:1 to 20:1 or higher has been found to advantageously increase the catalytic efficiency of the resulting chromium catalyst by providing similar polymer yields at lower catalyst concentrations in the polymerization reaction mixtures. In some embodiments the molar ratio is 2:1, in other embodiments 5:1, in other embodiments 10:1, in still other embodiments 20:1, and in still other embodiments >20:1 (e.g., ≤30:1).

The cocatalyst can be the oxidant cocatalyst. Preferably, the oxidant cocatalyst is a ferrocenium or trityl borate or an electrophile. Preferably, the ferrocenium borate is ferrocenium tetrakis(pentafluorophenyl)borate and the trityl borate is the TTB, and more preferably BOMATPB. Preferably, the electrophile is dichloromethane.

The term "preparation effective conditions" means environmental parameters such as solvent(s), atmosphere(s), temperature(s), pressure(s), time(s), and the like that are preferred for giving at least a 10 percent (%), more preferably at least 20%, and still more preferably at least 30% reaction yield of the relevant product from the relevant process after 10 hours reaction time. Preferably, the relevant process independently is run under an inert atmosphere (e.g., under an inert gas consisting essentially of, for example, nitrogen gas, argon gas, helium gas, or a mixture of any two or more thereof). Preferably, the relevant process is run with an aprotic solvent or mixture of two or more aprotic solvents, e.g., an ether and toluene. The reaction mixture may comprise additional ingredients such as those described previously herein. Preferably, the relevant process is run at a temperature of the reaction mixture of from −20° C. to 200° C. In some embodiments, the temperature is at least 0° C., and more preferably at least 20° C. In other embodiments, the temperature is 100° C. or lower, more preferably 50° C. or lower, and still more preferably 40° C. or lower. A convenient temperature is ambient temperature, i.e., from 20° C. to 30° C. Preferably the relevant invention process independently is run at ambient pressure, i.e., at 1 atm (e.g., from 95 kPa to 107 kPa, such as 101 kPa).

A preferred catalytically effective amount of any catalyst herein means mole percent (mol %) of the any catalyst for a catalyzed reaction that independently is less than 90 mol % of a number of moles of a product-limiting stoichiometric reactant employed in the catalyzed reaction and equal to or greater than a minimum mol % value that is necessary for at least some product of the catalyzed reaction to be formed and detected (e.g., by mass spectrometry), wherein 100 mol % is equal to the number of moles of the product-limiting stoichiometric reactant employed in the catalyzed reaction. The minimum catalytic amount preferably is 0.000001 mol %, and may be 0.00001 mol %, 0.0001 mol %, 0.001 mol %, or even 0.01 mol %. Preferably, the catalytic amount of each of the olefin polymerization catalysts independently is from 0.00001 mol % to 50 mol % of the moles of olefin monomer or comonomer, whichever is lower.

In another embodiment the present invention provides a first metal composition comprising at least 11 mole percent (mol %), in other embodiments at least 51 mol %, in other embodiments at least 91 mol %, and in still other embodiments >99 mol % (e.g., 100 mol %) of the complex of formula (J). In another embodiment the present invention provides a second metal composition comprising at least 1 mol % of the complex of formula (J) and at least 1 mol % of the metal-ligand complex suitable for preparing the SIOP catalyst, preferably the IOP Group 4 metal-ligand complex.

In some embodiments the first and second metal compositions independently further comprise, and the invention polymerization process further employs, an effective amount of a polymer yield-enhancing additive that functions to increase yield of the partially chain-straightened poly(1-alkene) or OBC by at least 5% compared to yield from an identical process except lacking the additive. Preferably, the additive is a ferrocenium or trityl borate or an alkyl halide (e.g., dichloromethane). Preferably, the ferrocenium borate is ferrocenium tetrakis(pentafluorophenyl)borate and the trityl borate is the BOMATPB. The polymer yield-enhancing additive is enhancing for the complex of formula (J). In some embodiments the additive and cocatalyst are the same, and in other embodiments are different. The effective amount of the additive can be a molar amount that is less than the number of moles of Cr metal employed, but preferably is any molar amount equal to or greater than the number of moles of Cr metal of the homogeneous chromium catalyst. For example, 1 milliliter (mL) of dichloromethane is a sufficient effective amount for the molar amount of homogeneous chromium catalyst that is typically employed in a 2 liter (L) reactor.

The olefin polymerization process can comprise a continuous, batch or semi-batch preparation method and run in gas phase or liquid (preferably solution) phase. A continuous process is preferred for preparing the OBC, in which continuous process, for example, chromium catalyst, straight chain 1-alkene, and optionally at least one of a olefin comonomer other than the same straight chain 1-alkene, CSA, SIOP catalyst, a solvent, diluent, and dispersant, or combination thereof are essentially continuously supplied to the reaction zone, and resulting PCS poly(1-alkene)-containing polyolefin product is essentially continuously removed therefrom. The olefin polymerization process can be carried out in a same reactor or in separate reactors (e.g., to make an OBC), preferably connected in series or in parallel, to prepare polymer blends having desirable properties. A general description of such a process is disclosed in WO 94/00500. In some embodiments the olefin polymerization is carried out according to the batch solution polymerization described later in the Examples or by adapting the high throughput parallel polymerization conditions described in paragraph [0338] or the continuous solution polymerization conditions described in paragraph [0349], all of US 2010/0298515 A1. Preferably for manufacturing, the PCS poly(1-alkene) is produced in a solution process, more preferably an essentially continuous solution process. While a polymer (polyolefin) produced in a polymerization reaction can be said to comprise a mixture of different polymer molecules, as used herein, the term "polymer blend" means a mixture of different polymer molecules prepared by two different polymerization reactions and not covalently bonded to each other.

As used herein, "olefin polymerizing conditions" independently refer to reaction conditions such as solvent(s), atmosphere(s), temperature(s), pressure(s), time(s), and the like that are preferred for giving at least a 10 percent (%), more preferably at least 20%, and still more preferably at least 30% reaction yield of the polyolefin (e.g., PCS poly(1-alkene)) after 15 minutes reaction time. Preferably, the polymerization processes independently are run under an inert atmosphere (e.g., under an inert gas consisting essentially of, for example, nitrogen gas, argon gas, helium gas, or a mixture of any two or more thereof). Other atmospheres are contemplated, however, and these include sacrificial olefin in the form of a gas. In some aspects, the polymerization processes independently are run without any solvent, i.e., is a neat polymerization process that is run in a neat mixture of aforementioned ingredients. In other aspects, the neat mixture further contains additional ingredients (e.g., catalyst stabilizer such as triphenylphosphine) other than solvent(s). Preferably, the polymerization processes independently are run with a solvent or mixture of two or more solvents (e.g., isoparaffinic hydrocarbons, toluene, dodecane, mesitylene, or a mixture thereof). Preferably, the polymerization process is run at a temperature of the reaction ingredients of from 0° C. to 200° C., and more preferably from 20° C. to 190° C. In some embodiments, the temperature is at least 40° C. In other embodiments, the temperature is 175° C. or lower, more preferably 150° C. or lower, and still more preferably 140° C. or lower. A convenient temperature is from 60° C. to 100° C., and more preferably from 80° C. to 90° C. In some embodiments, the polymerization processes independently run under a pressure of 1000 pounds per square inch (psi) or less, i.e., 70 atmospheres (atm) or 7000 kilopascals (kPa), or less. Preferably the polymerization processes independently run under a pressure of from 0.9 atm to 50 atm (i.e., from 91 kiloPascals (kPa) to 5000 kPa). A convenient pressure is from 3000 kPa to 4900 kPa. A convenient time for a polymerization is from 5 minutes to 8 hours.

Preferably in the invention polymerization processes, the olefin monomer comprises ethylene, an alpha-olefin, cyclic olefin (e.g., norbornene), aromatic olefin (e.g., styrene and divinyl benzene), or a cyclic or acyclic diene (e.g., norbornadiene or 1,3-butadiene respectively). Preferably, the olefin monomer is the alpha-olefin, more preferably a branched chain alpha-olefin, still more preferably a linear-chain alpha-olefin, even more preferably the straight chain 1-alkene having n carbon atoms. Preferably n is an integer of from 3 to 40, and thus the straight chain 1-alkene is a compound of formula (Z): $CH_2=CH_2-(CH_2)_tCH_3$ (Z), wherein t is an integer of from 0 to 37, and yet even more preferably a straight chain 1-alkene that is 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, a ($C_8$-$C_{40}$)alpha-olefin, or a linear-chain ($C_{20}$-$C_{24}$)alpha-olefin. More preferably, the 1-alkene is 1-propene or, still more preferably 1-butene. In some embodiments the process further employs an olefin comonomer, i.e., other than the olefin monomer. In some embodiments the olefin comonomer is a 1-alkene that is different than the 1-alkene employed for the olefin monomer. In other embodiments the olefin comonomer is ethylene. Preferably, the ethylene is employed in a weight percent (wt %) amount relative to 1-alkene (i.e., weight of ethylene divided by weight of 1-alkene, expressed as a percent) that is from 0.001 wt % to 30 wt %. In some embodiments the amount of ethylene relative to 1-alkene is at most 20 wt %, in other embodiments at most 15 wt %, in still other embodiments at most 12 wt %, and in still other embodiments at most 10 wt %. In some embodiments the amount of ethylene relative to 1-alkene is at least 0.1 wt %, in other embodiments at least 1 wt %, in still other embodiments at least 2 wt %, and in still other embodiments at least 5 wt %. In the PCS poly(1-alkene) or the PCS poly(1-alkene) atactic block of the OBC, an analytical technique such as ad rem methods of US 2010/0093964 A1 can be used to determine (a) the extent of block copolymer formation in the OBC, (b) the total mole percent of (ethylene residuals+$(CH_2)_n$ units) in the PCS poly(1-alkene) or the PCS poly(1-alkene) atactic block of the OBC, (c) the mole percent ethylene residuals in the syndiotactic or isotactic poly(1-alkene) block of the OBC, or (d) a combination of at least two of (a) to (c).

Advantageously, when the process for making the OBC further employs such amounts of ethylene, surprisingly incorporation of ethylene residual repeat units in the OBC predominantly is a function of catalysis by the homogeneous chromium catalyst. That is, the homogenous chromium catalyst has been unexpectedly found to be much more selective for ethylene than the SIOP catalyst. This selectivity means that the ethylene residual repeat units predominantly end up in the PCS poly(1-alkene) atactic block and not in the syndiotactic or isotactic poly(1-alkene) block of the OBC. Thus, the desired properties of the syndiotactic or isotactic poly(1-alkene) block can be advantageously preserved almost or just as if the process did not employ ethylene as the comonomer For example, the presence of ethylene in the process for making the OBC carried out in a continuous polymerization reactor does not markedly degrade melting point (i.e., does not decrease Tm by 20° C. or more) of the syndiotactic or isotactic poly(1-alkene) block, demonstrating that the chromium catalyst (e.g., chromium catalyst of the second embodiment) has a substantially greater affinity for ethylene than does the SIOP catalyst. Further, the ethylene polymerization selectivity discovered for the homogeneous chromium catalysts (e.g., the chromium catalyst of the second embodiment) advantageously enables a breakthrough in the preparation of an impact-modified poly(1-alkene), preferably an impact-modified polypropylene (IMPP), the breakthrough comprising preparing the impact-modified poly(l-alkene, preferably IMPP, in a single reactor according to the embodiment described previously.

Preferably for the process for selectively polymerizing ethylene, the reactivity ratio $r_1$ is greater than 20, more preferably greater than 30, still more preferably greater than 50, and even more preferably greater than 100. When the reactivity ratio $r_1$ for the invention processes approaches infinity, incorporation of the 1-alkene into the rich polyethylene produced thereby approaches 0 mol %. In some embodiments, the rich polyethylene, preferably the polyethylene hard segment of a poly(ethylene-co-1-alkene) block copolymer, is characterized as having 4 mol % or less, more preferably less than 2 mol %, and still more preferably 1.8 mol % or less of the residual of the 1-alkene covalently incorporated in the rich polyethylene or polyethylene hard segment of the poly(ethylene-co-1-alkene) block copolymer. In some embodiments, the rich polyethylene, preferably the polyethylene hard segment of the poly(ethylene-co-1-alkene) block copolymer is characterized as having at least 0.01 mol %, in other embodiments at least 0.1 mol %, and in still other embodiments at least 1.0 mol % of the residual of the (1-alkene covalently incorporated in the rich polyethylene or polyethylene hard segment of the poly(ethylene-co-1-alkene) block copolymer. Said mol % are preferably determined by NMR spectroscopy as described later. Preferably, the residuals of the 1-alkene and ethylene are approximately randomly distributed in the soft segment of the poly(ethylene-co-1-alkene) block copolymer.

In some embodiments that further employ ethylene in the process of the third embodiment for preparing the OBC, the polymerization that produces the PCS poly(1-alkene) atactic block of the OBC is characterized by a reactivity ratio $r_1$>10, preferably $r_1$>20, more preferably $r_1$>30, and still more preferably >50. Preferably in such embodiments, the polymerization that produces the syndiotactic or isotactic poly(1-alkene) block of the OBC is characterized by a reactivity ratio $r_1$<10, more preferably $r_1$<8, and still more preferably $r_1$<6.

Monomer and comonomer content of the polyolefins may be measured using any suitable technique such as, for example, IR spectroscopy and NMR spectroscopy, with $^{13}C$ NMR spectroscopy being preferred. Comonomer incorporation may be determined from the $^{13}C$ data using Randall's triad method (Randall, J. C.; JMS-Rev. Macromol. Chem. Phys., C29, 201-317 (1989.

In some embodiments, the amount of the 1-alkene (preferably, ($C_3$-$C_{40}$)alpha-olefin comonomer) incorporated into the rich polyethylene or the hard and soft segments of the poly(ethylene-co-1-alkene) block copolymer is characterized by a comonomer incorporation index. As used herein, the term, "comonomer incorporation index", refers to the mole percent of residuals of comonomer (1-alkene) incorporated into an ethylene/comonomer copolymer, or ethylene-derived hard segment thereof, prepared under representative olefin polymerization conditions (described later herein), ideally under steady-state, continuous solution polymerization conditions in a hydrocarbon diluent at 100° C., 4.5 megapascals (MPa) ethylene pressure (reactor pressure), greater than 92 percent (more preferably greater than 95 percent) ethylene conversion, and greater than 0.01 percent comonomer conversion. The selection of metal complexes or catalyst compositions having the greatest difference in comonomer incorporation indices results in copolymers from two or more monomers having the largest difference in block or segment properties, such as density.

Reactivity ratios $r_1$ for use in the foregoing models may be predicted using well known theoretical techniques or empirically derived from actual polymerization data. Suitable theoretical techniques are disclosed, for example, in B. G. Kyle, *Chemical and Process Thermodynamics*, Third Addition, Prentice-Hall, 1999 and in Redlich-Kwong-Soave (RKS) Equation of State, *Chemical Engineering Science,* 1972, pp 1197-1203. Commercially available software programs may be used to assist in deriving reactivity ratios from experimentally derived data. One example of such software is Aspen Plus from Aspen Technology, Inc., Ten Canal Park, Cambridge, Mass. 02141-2201 USA. Further description for determining reactivity ratio $r_1$ is found in US 2010/0331492 A1, including paragraphs [0095] to [0109].

In some embodiments the polyolefin produced in the invention process is, for example, a conventional polyolefin (e.g., polyethylene, poly(alpha-olefin), or, preferably, the PCS poly(1-alkene) or segment. The PCS poly(1-alkene) or segment comprises an atactic olefin interpolymer or segment that can be conveniently named by referring to the portion derived by 1,n-addition as ethylene and the portion derived by 1,2-addition as the 1-alkene. Examples of atactic olefin interpolymer or segment named in this way include any one of: ethylene/propylene (from invention process polymerizing propylene), ethylene/1-butene (from invention process polymerizing 1-butene), ethylene/1-pentene (from invention process polymerizing 1-pentene), ethylene/1-hexene (from invention process polymerizing 1-hexene), ethylene/1-heptene (from invention process polymerizing 1-heptene), ethylene/1-octene (from invention process polymerizing 1-octene), ethylene/propylene/styrene (from invention process copolymerizing 1-propylene and styrene), ethylene/propylene/butadiene (from invention process copolymerizing 1-propylene and butadiene), ethylene/propylene/hexadiene (from invention process copolymerizing 1-propylene and hexadiene), ethylene/propylene/ethylidenenorbornene (from invention process copolymerizing 1-propylene and ethylidenenorbornene), and other EPDM terpolymers. In some embodiments the PCS poly(1-alkene) comprises a non-block copolymer, and in other embodiments the atactic segment of the OBC.

Monomer and comonomer content, and 1,n- and 1,2-addition content, of the polyolefin prepared by the invention process may be measured using any suitable technique such as, for example, infrared (IR) spectroscopy, especially Fourier Transform (FT)-IR spectroscopy, and nuclear magnetic resonance (NMR) spectroscopy, with techniques based on proton and $^{13}C$ NMR spectroscopy as described later being respectively preferred and more preferred.

The number average molecular weight ($M_n$), weight average molecular weight ($M_w$), and polydispersity index (PDI, $M_w/M_n$) for the polyolefin can be determined by gel permeation chromatography (GPC) as described later. Preferably, the PCS poly(1-alkene) has a $M_w$ of from 50,000 grams per mole (g/mol) to 2,000,000 g/mol. In some embodiments the $M_w$ is at least 100,000 g/mol, in other embodiments at least 150,000 g/mol, and in other embodiments at least 160,000 g/mol. In some embodiments the $M_w$ is at most 1,000,000 g/mol, in other embodiments at most 900,000 g/mol, and in other embodiments at most 700,000 g/mol. In some embodiments the PCS poly(1-alkene) has a $M_n$ of from 5,000 grams per mole (g/mol) to 1,000,000 g/mol. In some embodiments the $M_n$ is at least 9,000 g/mol, in other embodiments at least 10,000 g/mol, and in other embodiments at least 30,000 g/mol. In some embodiments the $M_n$ is at most 400,000 g/mol, in other embodiments at most 300,000 g/mol, and in other embodiments at most 150,000 g/mol. In some embodiments the PCS poly(1-alkene) has a PDI of from 2.0 to 50 In some embodiments the PDI is at least 2.7, in other embodiments at least 3.5, and in other embodiments at least 8.0. In some embodiments the PDI is at most 20, in other embodiments at most 19, and in other embodiments at most 17.

Preparation 1: Preparation of Chromium Complex (a1)

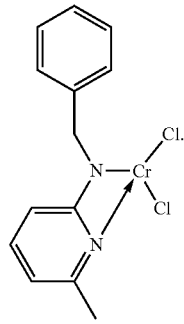

(a1)

Dissolve 11.06 millimoles (mmol) of 2-benzylamino-6-methylpyridine in 100 mL dry toluene, and add 11.6 mmol of a 1.87 M solution of PhLi (6.21 mL) in dibutyl ether all at once. Stir the resulting solution overnight. To the resulting mixture add 4.144 g (11.06 mmol) solid $CrCl_3(THF)_3$ all at once. Stir 9 hours, and then evaporate volatiles in vacuum to give respectively give complex (a1).

In some embodiments the present invention provides the compound or chromium complex prepared in any one of the foregoing preparations.

Some embodiments of the invention are described in more detail in the following Examples.

Example 1

Preparation of Chromium Complex (1)

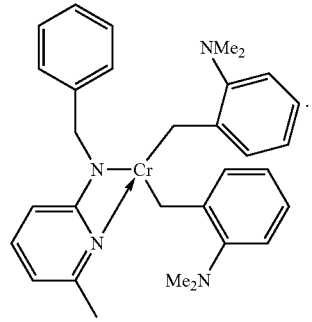

(1)

Add N-benzyl-6-methylpyridin-2-amine (7.603 g, 16.72 mmol) in benzene (100 mL) dropwise to a solution of chromium complex (a1) in benzene (200 mL) with stirring. Stir the mixture for an additional hour. Remove volatiles from the reaction mixture under vacuum, and dissolve the residue in hexane. Warm the solution to 60° C. for a short time to aid dissolution, filter through a combination frit 20 μm PE pre-frit and 1 μm PTFE final frit), and place the filtrate solution in the freezer (−10° C.) overnight, during which time red crystals form. Isolate the crystals by decanting of the liquid to give complex (1) (6.705 g, 77.5%). FIG. 1 depicts an ORTEP of a single crystal structure derived by x-ray analysis of invention complex (1) with hydrogen atoms omitted for clarity.

Example 2

Preparation of Chromium Complex (2)

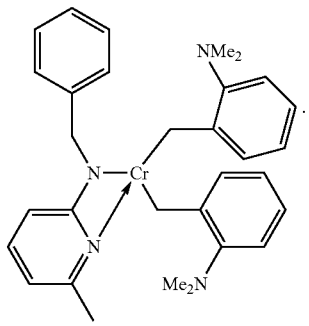

(2)

Figure 2:
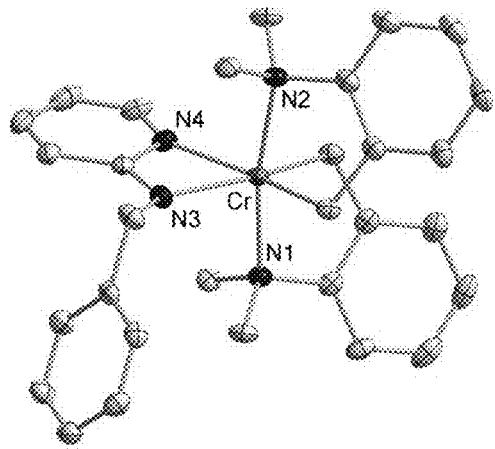
FIG. 2 depicts an ORTEP of a single crystal structure derived by x-ray analysis of invention complex (2) (Example 2) with hydrogen atoms omitted for clarity.

Add N-benzylpyridin-2-amine (0.173 g, 0.38 mmol) in D6-benzene (5 mL) dropwise to a solution of chromium complex (a1) in D6-benzene (5 mL) with stirring. NMR of an aliquot indicates that the reaction has already occurred since all that is observed free from Cr as evidenced by the diamagnatism is the N,N,2-trimethylaniline by-product. Remove volatiles from the reaction mixture under vacuum, and dissolve the residue in methylcyclohexane. Warm the solution to 60° C. for a short time to aid dissolution, filter through a combination frit 20 μm PE pre-frit and 1 μm PTFE final frit), and place the filtrate solution in the freezer (−10° C.) overnight, during which time red/brown crystals form. The Carefully dry the crystals by blowing $N_2$ gas over them for a short time to give complex (2). Obtain a second crop of crystals. Further drying of the material results in the isolation of complex (2) as a red/brown crystalline solid (0.106 g, 55.8%). Grow X-ray quality crystals from a hexane solution (−10° C.). FIG. 2 depicts an ORTEP of a single crystal structure derived by x-ray analysis of invention complex (2) with hydrogen atoms omitted for clarity.

Example 3

Preparation of Chromium Complex (3)

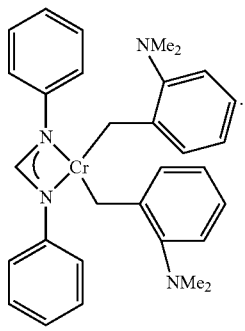

(3)

Figure 3:
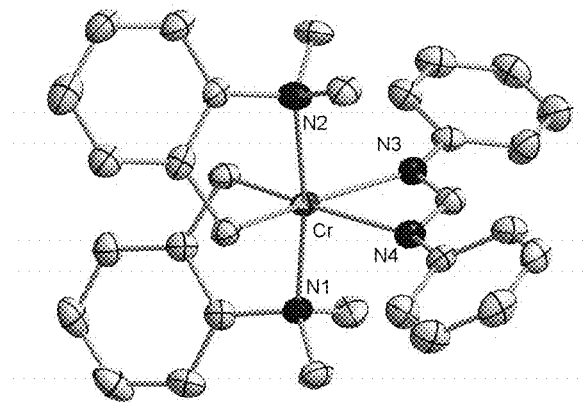
FIG. 3 depicts an ORTEP of a single crystal structure derived by x-ray analysis of invention complex (3) (Example 3) with hydrogen atoms omitted for clarity.

Add chromium complex (a1) (0.100 g, 0.22 mmol) and (E)-N,N'-diphenylformimidamide (0.043 g, 0.22 mmol) together in a reaction vessel as solids followed by D6-benzene (10 mL). The solids immediately dissolve. NMR analysis of the solution indicates that the reaction is complete. Remove volatiles from the reaction mixture under vacuum, and dissolve the residue in methylcyclohexane. Warm the solution to 50° C. for a short time to aid dissolution, filter through a combination frit 20 μm PE pre-frit and 1 μm PTFE final frit), and place the filtrate solution in the freezer (−10° C.) overnight. Clear red crystals precipitate and are isolated by decanting of the liquor. Dry the crystals carefully by blowing $N_2$ gas over them for a short time. Further drying of the material results in the isolation of complex (3) as a red crystalline solid (0.0642 g, 56.8%). FIG. 3 depicts an ORTEP of a single crystal structure derived by x-ray analysis of invention complex (3) with hydrogen atoms omitted for clarity.

Example 4

Preparation of Chromium Complex (4)

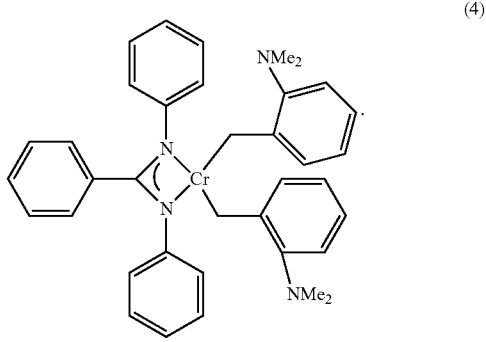

(4)

Figure 4:
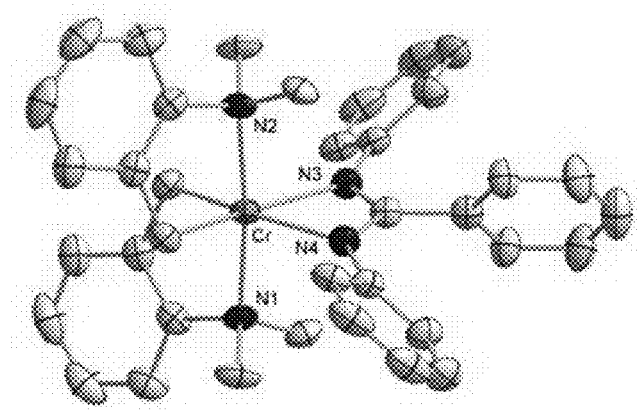
FIG. 4 depicts an ORTEP of a single crystal structure derived by x-ray analysis of invention complex (4) (Example 4) with hydrogen atoms omitted for clarity.

Add chromium complex (a1) (0.100 g, 0.22 mmol) and (E)-N,N'-diphenylbenzimidamide (0.302 g, 1.11 mmol) together in a reaction vessel as solids followed by D6-benzene (10 mL). The solids immediately dissolve. NMR analysis of the solution indicates that the reaction is complete. Remove volatiles from the reaction mixture under vacuum, and stir the residue in hexane. Warm the solution to 50° C. for a short time to aid dissolution, filter through a combination frit 20 μm PE pre-frit and 1 μm PTFE final frit), and place the filtrate solution in the freezer (−10° C.) overnight. Clear red crystals precipitate and are isolated by decanting of the liquor and drying them under vacuum to give complex (4) (0.0735 g, 11.2%). FIG. 4 depicts an ORTEP of a single crystal structure derived by x-ray analysis of invention complex (4) with hydrogen atoms omitted for clarity.

Example 5

Preparation of Chromium Complex (5)

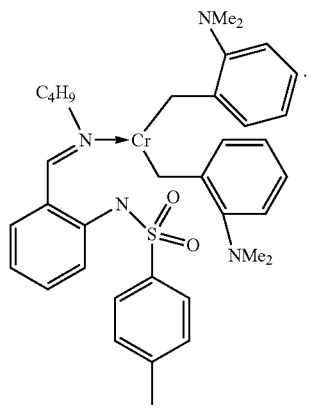

Figure 5:
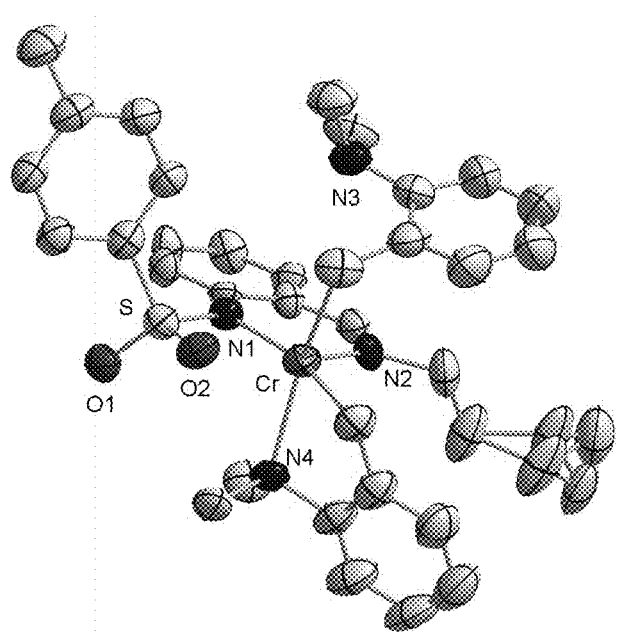
FIG. 5 depicts an ORTEP of a single crystal structure derived by x-ray analysis of invention complex (5) (Example 5) with hydrogen atoms omitted for clarity.

Add (E)-N-(2-((Butylimino)methyl)phenyl)-4-methylbenzenesulfonamide (0.373 g, 1.13 mmol) in D6-benzene (5 mL) to chromium complex (a1) in D6-benzene (5 mL) with stirring. NMR analysis of the solution indicates that the reaction is complete. Remove volatiles from the reaction mixture under vacuum, and stir the residue in methylcyclohexane. Warm the solution to 60° C. for a short time to aid dissolution, filter through a combination frit 20 μm PE pre-frit and 1 μm PTFE final frit), and place the filtrate solution in the freezer (−10° C.) overnight during which time an oily film forms on the insides of the vial. This is repeated with the solid residue which does not dissolve in the hexane using (in separate flasks) methylcyclohexane and toluene so there are three different recrystallization attempts with three different solvents. They all behave similarly with this oily film forming in the freezer (−10° C.) after each repeated filtration into clean vials. Also unsuccessful is leaving open the vials in the freezer for slow concentration. Various attempts are made over a 10 day period of time. Finally, the solutions are allowed to evaporate at room temperature to dryness. The hexane and toluene solutions result in dark oily residues. The methylcyclohexane solution, just prior dryness, shows the formation of some structure on the bottom of the vial (not enough to be the majority of product). The remaining methylcyclohexane solution is pipetted away and X-ray analysis oil immediately added to the residual crystals. X-ray analysis is successful on these crystals. The remaining fractions are recombined and the volatiles removed resulting in the isolation of the dark oil. This oil is then slurried well in hexane and filtered. The filtrate is stripped to dryness and a brown solid isolated (0.188 g, 25.6%). FIG. 5 depicts an ORTEP of a single crystal structure derived by x-ray analysis of invention complex (5) with hydrogen atoms omitted for clarity.

Example 6

General Procedure of Embodiment of High Throughput Workflow Preparation of Chromium Complexes, Catalysts Prepared Therefrom, and PCS Polypropylene Prepared Therewith

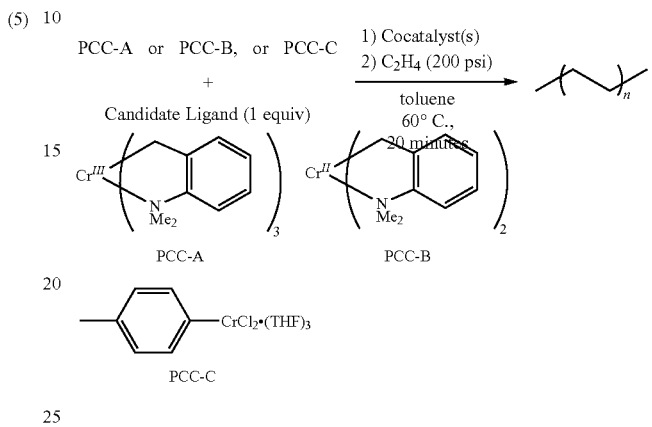

Add a 5 mM solution of penultimate chromium complex (PCC-A), (PCC-B), or (PCC-C) in toluene (200 μL) to a 5 mM solution of conjugate acid of ligand L in toluene (200 μL) and mix for 10 minutes at 60° C. Transfer a portion of the resulting candidate chromium complex solution (200 μL) to a vial containing cocatalyst TTB; FTPFPB; or BOMATPB/MMAO. For example, cocatalyst BOMATPB/MMAO includes 300 μL of 16.7 mM MMAO solution in toluene and 300 μL of 2 mM protic activating cocatalyst BOMATPB in toluene. Further dilute reaction mixture with 3030 μL toluene to give the resulting candidate chromium catalyst. Pressurize headspace to 200 psi with ethylene, and after mixing 20 minutes at 60° C., quench the reaction by addition of 300 μL of a 16.7 mM solution of benzoic acid-2,6-bis(1,1-dimethylethyl)-4-methylphenol (benzoic acid. BHT) in toluene. Remove volatiles from the quenchate under vacuum overnight, yielding polyethylene polymer.

Examples 7 to 31

High Throughput Workflow Preparation of Chromium Complexes, Catalysts Prepared Therefrom, and PCS Polypropylene Product Prepared Therewith Replicate the procedure of Example 6 with one of the structures of conjugate acid of ligand L shown in Table 1, and using each one of the following combinations of penultimate chromium complex and cocatalyst for each ligand L to give polyethylene products.

Combinations: Range of Yields of Polyethylene Product:
PCC-A+FTPFPB: 580 mg to 15 mg;
PCC-B+TTB: 13 mg to 0 mg (1 entry);
PCC-A+BOMATPB: 724 mg to 6 mg;
PCC-B+/MMAO: 363 mg to 11 mg;
PCC-A+TTB: 86 mg to 0 mg (1 run of 4);
PCC-C+FTPFPB: 159 mg to 8 mg;
PCC-A+/MMAO: 359 mg to 10 mg;

PCC-C+BOMATPB: 232 mg to 5 mg;
PCC-B+FTPFPB: 252 mg to 9 mg;
PCC-C+TTB: 22 mg to 1.6 mg; and
PCC-B+BOMATPB: 401 mg to 3 mg;
PCC-C+/MMAO: 639 mg to 13 mg.

TABLE 1

| Ligand used in Ex. No. | Structure of conjugate acid of ligand L |
|---|---|
| 7 | pyrrole-CH=N-CH₂CH₂-NMe₂ |
| 8 | 2-pyridyl-C(Ph)(Ph)-OH |
| 9 | 2-(MeSO₂NH)-C₆H₄-CH=N-CH₂Ph |
| 10 | pyrrole-CH=N-CH₂CH₂-OMe |
| 11 | pyrrole-CH=N-CH₂CH₂-SMe |
| 12 | pyrrole-CH=N-CH₂CH₂-SBn |
| 13 | indole-2-CH=N-CH₂CH₂-NMe₂ |
| 14 | pyrrole-CH=N-CH₂CH₂-PPh₂ |
| 15 | pyrrole-CH=N-CH₂CH₂-PiPr₂ |
| 16 | pyrrole-CH=N-CH₂CH₂-(1-pyrrolidinyl) |
| 17 | pyrrole-CH=N-CH₂CH₂-(1-piperidinyl) |
| 18 | 1-(methylamino)isoquinoline |
| 19 | 6-(1-naphthyl)-2-(2,6-diisopropylphenyl-N=CH)-pyridine |
| 20 | 6-(4-chlorophenyl)-2-((2,6-diisopropyl-4-chlorophenyl)-N=CH)-pyridine |
| 21 | 2-pyridyl-CH₂-NH-CH(Me)-C(Me)=N-OH |

TABLE 1-continued

| Ligand used in Ex. No. | Structure of conjugate acid of ligand L |
|---|---|
| 22 | [structure] |
| 23 | [structure] |
| 24 | [structure] |
| 25 | [structure] |
| 26 | [structure] |
| 27 | [structure] |
| 28 | [structure] |
| 29 | [structure] |
| 30 | [structure] |
| 31 | [structure] |

Names of conjugate acids of ligands L used in Examples 7 to 31 are as follows: N1-((1H-pyrrol-2-yl)methylene)-N2,N2-dimethylethane-1,2-diamine (used in Ex. 7); diphenyl(pyridin-2-yl)methanol (used in Ex. 8); N-(2-((benzylimino)methyl)phenyl)methanesulfonamide (used in Ex. 9); N-((1H-pyrrol-2-yl)methylene)-2-methoxyethanamine (used in Ex. 10); N-((1H-pyrrol-2-yl)methylene)-2-(methylthio)ethanamine (used in Ex. 11); N-((1H-pyrrol-2-yl)methylene)-2-(benzylthio)ethanamine (used in Ex. 12); N1-((1H-indol-2-yl)methylene)-N2,N2-dimethylethane-1,2-diamine (used in Ex. 13); N-((1H-pyrrol-2-yl)methylene)-2-(diphenylphosphino)ethanamine (used in Ex. 14); N-((1H-pyrrol-2-yl)methylene)-2-(di(propan-2-yl)phosphino)ethanamine (used in Ex. 15); N-((1H-pyrrol-2-yl)methylene)-2-(pyrrolidin-1-yl)ethanamine (used in Ex. 16); N-((1H-pyrrol-2-yl)methylene)-2-(piperidin-1-yl)ethanamine (used in Ex. 17); N-methylisoquinolin-1-amine (used in Ex. 18); 2,6-di(propan-2-yl)-N-((6-(naphthalen-1-yl)pyridin-2-yl)methylene)aniline (used in Ex. 19); 4-chloro-N-((6-(4-chlorophenyl)pyridin-2-yl)methylene)-2,6-di(propan-2-yl)aniline (used in Ex. 20); 3-((pyridin-2-ylmethyl)amino)butan-2-one oxime (used in Ex. 21); 4-methyl-N-(2-(((4-methylphenyl)imino)methyl)phenyl)-benzenesulfonamide (used in Ex. 22); N-(2-((butylimino)methyl)phenyl)-4-methylbenzenesulfonamide (used in Ex. 23); N-(2-((benzylimino)methyl)phenyl)-4-methylbenzenesulfonamide (used in Ex. 24); N-(2-((benzylimino)methyl)phenyl)-2,4,6-tri(propan-2-yl)benzenesulfonamide (used in Ex. 25); 9-(4-methoxypyrimidin-5-yl)-9H-xanthen-9-ol (used in Ex. 26); bis(4-methoxypyrimidin-5-yl)(phenyl) methanol (used in Ex. 27); bis(4-ethoxypyrimidin-5-yl)(phenyl)methanol (used in Ex. 28); 1-(2-ethoxy-6-methoxyphenyl)-2-methyl-1-phenylpropan-1-ol (used in Ex. 29); N-([1,1'-biphenyl]-2-yl(6-naphthalen-1-yl)pyridin-2-yl) methyl-2,6-di(propan-2-yl)aniline (used in Ex. 30); and N-benzyl-6-methylpyridin-2-amine (used in Ex. 31).

Illustrative preparations of some of the aforementioned conjugate acids of ligands L shown in Table 1 are as follow.

N1-((1H-pyrrol-2-yl)methylene)-N2,N2-dimethylethane-1,2-diamine ((conjugate acid of ligand used in Ex. No. 7): Dissolve 1 g (10.515 mmol) of pyrrole-2-carbaldehyde in 25 mL of dichloromethane (DCM) in a 40 mL glass vial with stirrer bar. Add 1 g (7.04 mmol) of $Na_2SO_4$ and then add 1.263 mL (11.567 mmol, p=0.8070 $gcm^{-3}$) of $N^1,N^1$-dimethylethane-1,2-diamine neat via syringe and stirring out for 24 hours. Monitor the reaction by GC-MS, whereby complete conversion to the desired product is observed. Filter the reaction mixture through a 0.2 μm polypropylene filter containing silica gel, wash the filtercake with 2×5 mL DCM, and concentrate the filtrate and washings in vacuo to give 1.725 g of N1-((1H-pyrrol-2-yl)methylene)-N2,N2-dimethylethane-1,2-diamine as a pale yellow oil, which is analytically pure by GC-MS & $^1$H-NMR: $^1$H NMR (400 MHz, Benzene) δ 10.70-10.26 (b, 1H), 7.82 (d, J=0.7 Hz, 1H), 6.64-6.50 (m, 1H), 6.45 (dd, J=3.5, 1.4 Hz, 1H), 6.24 (dd, J=3.5, 2.6 Hz, 1H), 3.53 (td, J=7.1, 1.2 Hz, 2H), 2.51 (t, 2H), 2.11 (s, 6H).

Diphenyl(pyridin-2-yl)methanol (conjugate acid of ligand used in Ex. No. 8): Stir a solution of 2-bromopyridine (25.00 g, 158 mmol) in THF (300 mL) under a nitrogen atmosphere at −78° C. Add a solution of n-BuLi (174.0 mmol, 69.62 mL of 2.5 M in hexanes) over a 50 minute period of time, during which time period the solution turns deep red. While maintaining the −78° C. temperature, stir the solution for an additional 1.5 hours. Then add a solution of benzophenone (28.83 g, 158.2 mmol) in THF (50 mL) over a 50 minute period of time resulting in a dark green mixture. Then allow the reaction mixture to warm to room temperature while stirring overnight. Quench the reaction mixture by the addition of a 0.25% aqueous solution of NaOH (200 mL). Separate the resulting aqueous layer, and wash it with diethyl ether (100 mL). Combine the organic layers, and wash the combination with water (200 mL), and dry over sodium sulfate. Remove the volatiles under vacuum. Add diethyl ether (2 mL) to the resulting residue, and scratch the flask with a spatula resulting in the precipitation of diphenyl(pyridin-2-yl)methanol as a light brown solid, which is washed with hexane (3×50 mL) and dried under vacuum (27.50 g, 69.2%). $^1$H NMR (500 MHz, $CDCl_3$) δ 8.58 (d, J=4.9 Hz, 1H), 7.62 (td, J=7.7, 1.7 Hz, 1H), 7.34-7.23 (m, 10H), 7.21 (dd, J=7.5, 4.9 Hz, 1H), 7.10 (d, J=8.0 Hz, 1H), 6.26 (s, 1H). $^{13}$C NMR (126 MHz, $CDCl_3$) δ 163.27, 147.74, 146.15, 136.37, 128.16, 127.92, 127.30, 122.91, 122.33, 80.86. GC/MS (CI): m/z (%): 262 (30) $[M+H]^+$, 244 (100) $[M+H-H_2O]^+$.

N-(2-((benzylimino)methyl)phenyl)methanesulfonamide (conjugate acid of ligand used in Ex. No. 9): Run reaction in a 35-mL microwave tube with magnetic stir bar. Heat N-(2-formylphenyl)methanesulfonamide (0.5004 g, 2.512 mmol), ethanol (12.0 mL), benzylamine (2.8 mL, 25.63 mmol), and a couple of crystals of p-toluenesulfonic acid to 75° C. for 2 hours on the microwave reactor, monitoring the reaction by GC/MS. Place the resulting solution in a freezer (−10° C.) for 3 days, and observe crystallization. Collect crystalline solid by filtration while it is cold, wash the collected solid with small portions of cold ethanol, and dry under vacuum to afford 0.2617 mg (36.1%) of N-(2-((benzylimino)methyl) phenyl)methanesulfonamide as a crystalline yellow solid.

N-((1H-pyrrol-2-yl)methylene)-2-methoxyethanamine (conjugate acid of ligand used in Ex. 10): Replicate the preparation of the ligand used in Ex. 7 except use 1.004 mL (11.567 mmol, p=0.865 $gcm^{-3}$) of 2-methoxyethanamine instead of $N^1,N^1$-dimethylethane-1,2-diamine to give 1.585 g of N-((1H-pyrrol-2-yl)methylene)-2-methoxyethanamine as a pale yellow oil, which is analytically pure by GC-MS & $^1$H-NMR: $^1$H NMR (400 MHz, $CDCl_3$) δ 9.68-9.42 (b, 1H), 7.99 (d, J=0.7 Hz, 1H), 6.76 (d, J=1.2 Hz, 1H), 6.38 (dd, J=3.6, 1.4 Hz, 1H), 6.13 (dd, J=3.5, 2.8 Hz, 1H), 3.61 (t, J=5.4 Hz, 2H), 3.51 (t, J=8.2, 3.1 Hz, 2H), 3.27 (s, 3H).

N-((1H-pyrrol-2-yl)methylene)-2-(methylthio)ethanamine (conjugate acid of ligand used in Ex. 11): Replicate the preparation of the ligand used in Ex. 7 except use 0.928 g (9.758 mmol) of the pyrrole-2-carbaldehyde and 0.999 mL (10.734 mmol, p=0.980 $gcm^{-3}$) of 2-(methylthio)ethylamine instead of $N^1,N^1$-dimethylethane-1,2-diamine to give 1.62 g (98%) of N-((1H-pyrrol-2-yl)methylene)-2-(methylthio) ethanamine as a pale yellow oil, which is analytically pure by GC-MS & $^1$H-NMR: $^1$H NMR (400 MHz, $CDCl_3$) δ 9.45 (s, br, 1H), 7.99 (s, 1H), 6.78 (s, 1H), 6.40 (d, J=1.9 Hz, 1H), 6.14 (s, 1H), 3.64 (t, J=6.9 Hz, 2H), 2.66 (t, J=6.9 Hz, 2H), 2.04 (s, 3H).

N-((1H-pyrrol-2-yl)methylene)-2-(benzylthio)ethanamine (conjugate acid of ligand used in Ex. 12): Replicate the preparation of the ligand used in Ex. 7 except use 2.24 g (11.041 mmol) of 2-(benzylthio)ethanaminium chloride with 2 mL of triethylamine (14.347 mmol) instead of $N^1,N^1$-dimethylethane-1,2-diamine to give 2.364 g (92%) of N-((1H-pyrrol-2-yl)methylene)-2-(benzylthio)ethanamine as a pale yellow, semi solid, which is analytically pure by GC-MS & $^1$H-NMR: $^1$H NMR (400 MHz, $CDCl_3$) δ 9.77-9.10 (s, br 1H), 7.89 (d, J=0.8 Hz, 1H), 7.20-7.16 (m, 3H), 7.14-7.07 (m, 2H), 6.73 (dd, J=1.8, 0.8 Hz, 1H), 6.37 (dd, J=3.6, 1.4 Hz, 1H), 6.11 (dd, J=3.6, 2.7 Hz, 1H), 3.60 (s, 2H), 3.54 (td, J=6.9, 1.1 Hz, 2H), 2.56 (t, J=6.9 Hz, 2H).

N1-((1H-indol-2-yl)methylene)-N2,N2-dimethylethane-1,2-diamine (conjugate acid of ligand used in Ex. 13): Replicate the preparation of the ligand used in Ex. 7 except use 0.200 g (1.378 mmol) of 1H-indole-2-carbaldehyde instead of pyrrole-2-carbaldehyde and use 0.158 mL (1.447 mmol) of the $N^1,N^1$-dimethylethane-1,2-diamine to give 0.285 g (96%) of N1-((1H-indol-2-yl)methylene)-N2,N2-dimethylethane-1,2-diamine as an off-white solid, which is analytically pure by GC-MS and $^1$H-NMR: $^1$H NMR (400 MHz, $CDCl_3$) δ 9.11 (s, br, 1H), 8.19 (s, br, 1H), 7.53 (d, J=7.8 Hz, 1H), 7.23 (d, J=8.0 Hz, 1H), 7.14 (t, J=8.0 Hz, 1H), 7.00 (t, J=7.4 Hz, 1H), 6.65 (s, br, 1H), 3.64 (t, J=6.3 Hz, 2H), 2.53 (t, J=6.7 Hz, 2H), 2.22 (s, 6H).

N-((1H-pyrrol-2-yl)methylene)-2-(diphenylphosphino) ethanamine (conjugate acid of ligand used in Ex. 14): Replicate the preparation of the ligand used in Ex. 7 except use 0.2 g (2.103 mmol) of pyrrole-2-carbaldehyde and use 0.506 g (2.208 mmol) of 2-(diphenylphosphino)ethanamine instead of $N^1,N^1$-dimethylethane-1,2-diamine to give 0.640 g (99%) of N-((1H-pyrrol-2-yl)methylene)-2-(diphenylphosphino) ethanamine as a white solid, which is analytically pure by GC-MS and $^1$H-NMR: $^1$H NMR (400 MHz, $C_6D_6$) δ 9.49 (s, 1H), 7.62 (s, 1H), 7.49-7.32 (m, 5H), 7.11-6.92 (m, 5H), 6.44-6.29 (m, 2H), 6.22-6.14 (m, 1H), 3.58 (td, J=8.8, 1.0 Hz, 2H), 2.37 (dd, J=8.4, 7.1 Hz, 2H).

N-((1H-pyrrol-2-yl)methylene)-2-(di(propan-2-yl)phosphino)ethanamine (conjugate acid of ligand used in Ex. 15): Replicate the preparation of the ligand used in Ex. 7 except use 0.2 g (2.103 mmol) of pyrrole-2-carbaldehyde and use adding 0.356 g (2.208 mmol) of 2-(di-isopropylphosphino) ethanamine instead of $N^1,N^1$-dimethylethane-1,2-diamine to give 0.487 g (97%) of N-((1H-pyrrol-2-yl)methylene)-2-(di (propan-2-yl)phosphino)ethanamine as a colorless, semi solid, which is analytically pure by GC-MS and $^1$H-NMR: $^1$H NMR (400 MHz, Benzene): δ 10.05 (s, 1H), 7.83 (s, 1H), 6.51 (s, 1H), 6.44 (m, J=2.2 Hz, 1H), 6.28-6.14 (m, 1H), 3.67 (dd, J=15.2, 6.9 Hz, 2H), 1.75-1.64 (m, 2H), 1.58 (dq, J=6.9, 5.3 Hz, 2H), 1.00 (ddd, J=14.8, 12.3, 7.1 Hz, 12H).

N-((1H-pyrrol-2-yl)methylene)-2-(pyrrolidin-1-yl)ethanamine (conjugate acid of ligand used in Ex. 16): Replicate the preparation of the ligand used in Ex. 7 except use 1.399 mL (11.041 mmol, ρ=0.901 gcm$^{-3}$) of 2-(pyrrolidin-1-yl) ethanamine instead of $N^1,N^1$-dimethylethane-1,2-diamine to give 1.97 g (98%) of N-((1H-pyrrol-2-yl)methylene)-2-(pyrrolidin-1-yl)ethanamine as a pale yellow oil, which is analytically pure by GC-MS and $^1$H-NMR: $^1$H NMR (400 MHz, CDCl$_3$) δ 9.94 (s, 1H), 8.12 (s, 1H), 6.88 (s, 1H), 6.64-6.38 (m, 1H), 6.37-5.97 (m, 1H), 3.72 (t, J=6.7 Hz, 2H), 2.84-2.67 (m, 2H), 2.58 (s, 4H), 1.79 (s, 4H).

N-((1H-pyrrol-2-yl)methylene)-2-(piperidin-1-yl)ethanamine (conjugate acid of ligand used in Ex. 17): Replicate the preparation of the ligand used in Ex. 7 except use 1.575 mL (11.041 mmol, ρ=0.899 gcm$^{-3}$) of 2-(piperidin-1-yl) ethanamine instead of $N^1,N^1$-dimethylethane-1,2-diamine to give 2.12 g (98%) of N-((1H-pyrrol-2-yl)methylene)-2-(piperidin-1-yl)ethanamine as a pale yellow oil, which is analytically pure by GC-MS and $^1$H-NMR: $^1$H NMR (400 MHz, CDCl$_3$) δ 9.95 (s, 1H), 8.10 (s, 1H), 6.88 (s, 1H), 6.56-6.38 (m, 1H), 6.35-6.07 (m, 1H), 3.71 (t, J=6.9 Hz, 2H), 2.68-2.55 (m, 2H), 2.47 (m, br, 4H), 1.70-1.52 (m, 4H), 1.45 (m, J=4.3 Hz, 2H).

N-methylisoquinoline-1-amine (conjugate acid of ligand used in Ex. No. 18:) is synthesized inside a glovebox by suspending sodium hydride (161 mg, 6.71 mmol) in THF (5.0 mL), dissolving 1-aminoisoquinoline (967 mg, 6.71 mmol, 1.0 eq) in 3 mL THF, and adding it to the sodium hydride suspension. Heat the resulting mixture to 40° C. for 30 minutes, then cool to −25° C. with a precooled copper bath. Add methyl iodide (980 mg, 1.82 mmol, 1.05 eq) in THF (3.0 mL), and stir the resulting mixture at room temperature overnight. Add water, and extract the resulting aqueous mixture several times with ethyl acetate. Combine and dry the extracts over magnesium sulfate, filter, and concentrate under reduced pressure to give N-methylisoquinoline-1-amine (990 mg, 6.26 mmol, 93%) as a colorless solid. $^1$H NMR (500 MHz, CDCl$_3$) δ 8.03 (d, J=5.9 Hz, 1H), 7.72 (d, J=8.3 Hz, 1H), 7.66 (d, J=8.1 Hz, 1H), 7.56 (dd, J=8.1, 7.0 Hz, 1H), 7.43 (dd, J=8.3, 7.0 Hz, 1H), 6.92 (d, J=5.9 Hz, 1H), 5.34 (br, 1H), 3.16 (d, J=4.8 Hz, 3H); $^{13}$C NMR (126 MHz, CDCl$_3$) δ 155.82, 141.44, 136.93, 129.56, 127.14, 125.79, 121.31, 118.27, 110.73, 28.83. GC/MS (Cr, methane): m/z=159 (100%, M+H$^+$), 160 (12.9%), 187 (24.1%, M+C$_2$H$_9^+$).

Examples 32 to 56 replicate Preparation 1 twenty-five times except each time use a different one of the conjugate acids of ligands used in Examples 7 to 31, respectively, shown in Table 1 instead of 2-benzylamino-6-methylpyridine to respectively give chromium dichloride complexes of Examples 32a to 56a wherein the complexes also contain as a bidentate ligand L the anionic form (i.e., conjugate base form) of the ligands listed in Table 1.

Examples 57 to 81

Dimethyl chromium complexes and Examples 82 to 106 dibenzyl chromium complexes: In 2×25 separate runs, dissolve 0.30 millimoles (mmol) a different one of the chromium dichloride complexes of Examples 32 to 56 in toluene (20 mL), and cool the solution in a drybox freezer for 30 minutes. Then add dropwise either a 3 molar (M) solution of CH$_3$MgBr (0.2 mL, 0.59 millimoles (mmol)) in diethyl ether (Examples 57-81) or a 1 M solution of PhCH$_2$MgCl (0.6 mL, 0.6 mmol) in diethyl ether (Examples 82-106) with stirring. Stir overnight at room temperature (25° C.), filter through a syringe filter (0.45 μm), and evaporate filtrate to dryness under vacuum to give a solid. Further purification: mix solid with 5 mL benzene, filter, and evaporate filtrate as before to give the dimethyl chromium complexes of Examples 57 to 81, respectively, wherein the complexes also contain as a bidentate ligand L the anionic form (i.e., conjugate base form) of the ligands listed in Table 1 and the dibenzyl chromium complexes of Examples 82 to 106, respectively, wherein the complexes also contain as a bidentate ligand L the anionic form (i.e., conjugate base form) of the conjugate acid of ligands L listed in Table 1.

Examples 107 to 206

Replicate Example 6 at least 100 times with at least 100 additional different ligands and find that they can be contacted with PCC-A, PCC-B, or PCC-C to produce chromium complexes of Examples 107 to 206, that the chromium complexes of Examples 107 to 206 can be activated with TTB; FTPFPB; or BOMATPB/MMAO to prepare chromium catalysts of Examples 107 to 206, and that the chromium catalysts of Examples 107 to 206 can be contacted with ethylene to prepare polyethylene.

Examples 207 to 216

Replicate Example 6 ten times with a different one of the following conjugate acids of ligands and find that they can be contacted with PCC-A, PCC-B, or PCC-C to produce chromium complexes of Examples 107 to 216, that the chromium complexes of Examples 107 to 216 can be activated with TTB; FTPFPB; or BOMATPB/MMAO to prepare chromium catalysts of Examples 107 to 216, and that the chromium catalysts of Examples 107 to 216 can be contacted with ethylene to prepare polyethylene. The catalyst of Ex. 212 prepares as much as 124 mg of polypropylene.

Names of conjugate acids of ligands L used in Examples 207 to 216 are as follows: $N^1$-(isoquinolin-1-yl)-$N^2,N^2$-dimethylethane-1,2-diamine (used in Ex. 207); N-(2-methoxyethyl)isoquinolin-1-amine (used in Ex. 208); $N^1$-(isoquinolin-1-yl)-$N^3,N^3$-dimethylpropane-1,3-diamine (used in Ex. 209); N-((tetrahydrofuran-2-yl)methyl)isoquinolin-1-amine (used in Ex. 210); $N^1$-(isoquinolin-1-yl)-$N^3,N^3$,2,2-tetramethylpropane-1,3-diamine (used in Ex. 211); 2,3-dihydro-1H-pyrrolo[2,3-b]pyridine (used in Ex. 212); N-(furan-2-ylmethyl)isoquinolin-1-amine (used in Ex. 213); 1,2-dihydropyrrolo[4,3,2-ij]isoquinoline (used in Ex. 214); 2,3-dihydro-1H-benzo[de][1,8]naphthyridine (used in Ex. 215); and N,N'-Diphenylbenzamidine (used in Ex. 216).

Structures of the conjugate acids of ligands L used in Examples 207-216 are shown below in Table 2.

TABLE 2

| used in Ex. No. | Structure of conjugate acid of ligand L |
|---|---|
| 207 | (isoquinoline with NH-CH2CH2-N(CH3)2 substituent) |
| 208 | (isoquinoline with NH-CH2CH2-O-CH3 substituent) |
| 209 | (isoquinoline with NH-CH2CH2CH2-N(CH3)2 substituent) |
| 210 | (isoquinoline with NH-CH2-tetrahydrofuryl substituent) |
| 211 | (isoquinoline with NH-C(CH3)2-CH2-N(CH3)2 substituent) |
| 212 | (7-azaindoline) |

TABLE 2-continued

| used in Ex. No. | Structure of conjugate acid of ligand L |
|---|---|
| 213 | (isoquinoline with NH-CH2-furyl substituent) |
| 214 | (fused tricyclic isoquinoline with NH-CH2 bridge) |
| 215 | (fused tricyclic isoquinoline with NH-CH2CH2 bridge) |
| 216 | Ph-NH-C(=N-Ph)-NH-Ph |

Ph means phenyl.

Illustrative preparations of some of the aforementioned conjugate acids of ligands L shown in Table 2 are as follow.

Conjugate acids of ligands used in Examples 207-211: In five 15 mL microwave tubes with stir bar, dissolve 1-chloroisoquinoline (5×500 mg, 3.06 mmol) in the corresponding amine (18.3 mmol, 6 eq,). Heat the mixtures in a CEM microwave reactor as indicated in Table 3. Work up the reaction mixtures by diluting them with 10-20 mL of diluted aqueous $NaHCO_3$ solution, and extracting each of the diluted mixtures with 20 mL of ethyl acetate (EtOAc). Dry the organic extracts over $MgSO_4$, filter, concentrate on the rotary evaporator at 80° C. (<1 Torr) in order to remove excess starting amine. If necessary, feed chloroform to the distillation as an aid for azeotropic removal of trace starting material. Keep the resulting ligands under high vacuum for several days and characterize them by GC/MS and NMR to give isolated ligands in purities of >95% and which can be used to form their chromium complexes without further purification.

TABLE 3

| For Ex. No. | Starting amine | structure of conjugate acid of ligand L | Reaction conditions | Appearance | Yield |
|---|---|---|---|---|---|
| 207 | (CH3)2N-CH2CH2-NH2 | (isoquinoline with NH-CH2CH2-N(CH3)2) | 160° C., 11 minutes | yellow oil | 82.6% |

TABLE 3-continued

| For Ex. No. | Starting amine | structure of conjugate acid of ligand L | Reaction conditions | Appearance | Yield |
|---|---|---|---|---|---|
| 208 | methoxyethylamine (CH₃OCH₂CH₂NH₂) | 1-(2-methoxyethylamino)isoquinoline | 160° C., 11 minutes | yellow oil | 83.4% |
| 209 | 3-(dimethylamino)propylamine | 1-[3-(dimethylamino)propylamino]isoquinoline | 160° C., 11 minutes | yellow oil | 83.1% |
| 210 | (tetrahydrofuran-2-yl)methylamine | 1-[(tetrahydrofuran-2-yl)methylamino]isoquinoline | 160° C., 14 minutes | yellow oil | 89.9% |
| 211 | 3-(dimethylamino)-2,2-dimethylpropylamine | 1-[3-(dimethylamino)-2,2-dimethylpropylamino]isoquinoline | 160° C., 6 minutes; then 180° C., 8 minutes | yellow oil | 82.9% |

Conjugate acid of ligand used in Ex. No. 207: $^1$H NMR (500 MHz, CDCl$_3$) δ 7.99 (d, J=5.9 Hz, 1H), 7.82 (d, J=8.4, 1H), 7.65 (d, J=8.1 Hz, 1H), 7.56 (dd, J=8.1, 6.9, 1H), 7.45 (dd, J=8.4, 6.9, 1H), 6.90 (d, J=5.9 1H), 6.06 (s, 1H), 3.63 (m, 2H), 2.65 (t, J=5.9 Hz, 2H), 2.31 (s, 6H); $^{13}$C NMR (126 MHz, CDCl$_3$) δ 155.43, 141.51, 136.99, 129.56, 126.98, 125.70, 121.82, 118.37, 110.57, 57.96, 45.23, 38.90; GC/MS (CI$^+$, methane): m/z=216 (100%, M+H$^+$), 217 (12.9%), 244 (17.1%, M+C$_2$H$_9$$^+$), 171 (77%).

Conjugate acid of ligand used in Ex. No. 208: $^1$H NMR (500 MHz, CDCl$_3$) δ 7.98 (d, J=5.9 Hz, 1H), 7.78 (d, J=8.4 Hz, 1H), 7.66 (d, J=8.1 Hz, 1H), 7.56 (dd, J=8.1, 6.9, 1H), 7.44 (dd, J=8.4, 6.9 Hz, 1H), 6.92 (d, J=5.9 Hz, 1H), 5.67 (s, 1H), 3.82 (m, 2H), 3.69 (t, J=5.3 Hz, 2H); $^{13}$C NMR (126 MHz, CDCl$_3$) δ 155.14, 141.30, 137.06, 129.61, 127.08, 125.80, 121.58, 118.29, 110.95, 71.37, 58.77, 41.30; GC/MS (CI$^+$, methane): m/z=203 (100%, M+H$^+$), 204 (15.0%), 231 (16.4%, M+C$_2$H$_9$$^+$), 171 (77%).

Conjugate acid of ligand used in Ex. No. 209: $^1$H NMR (500 MHz, CDCl$_3$) δ 7.97 (d, J=5.9 Hz, 1H), 7.69 (d, J=8.3, 1H), 7.63 (d, J=8.1 Hz, 1H), 7.59-7.55 (br, 1H), 7.54 (dd, J=8.1, 6.9 Hz, 1H), 7.41 (dd, J=8.3, 6.9 Hz, 1H), 6.85 (d, J=5.9 Hz, 1H), 3.69 (td, J=6.0, 4.5 Hz, 2H), 2.54 (t, J=6.0 Hz, 2H), 2.34 (s, 6H), 1.87 (q, J=6.0 Hz, 2H); $^{13}$C NMR (126 MHz, cdcl$_3$) δ 155.88, 141.73, 137.05, 129.35, 126.91, 125.57, 121.84, 118.60, 109.88, 59.72, 45.62, 42.70, 25.47; GC/MS (CI$^+$, methane): m/z=230 (86.5%, M+H$^+$), 258 (16.4%, M+C$_2$H$_9$$^+$), 185 (M-NHMe$_2$+H$^+$100%).

Conjugate acid of ligand used in Ex. No. 210: $^1$H NMR (500 MHz, CDCl$_3$) δ 7.97 (d, J=5.9 Hz, 1H), 7.80 (d, J=8.3 Hz, 1H), 7.65 (d, J=8.1 Hz, 1H), 7.56 (ddd, J=8.1, 6.9 Hz, 1H), 7.44 (dd, J=8.3, 6.9 Hz, 1H), 6.92 (d, J=5.9 Hz, 1H), 5.67 (br, 1H), 4.23 (dtd, J=7.8, 7.0, 3.2 Hz, 1H), 3.98-3.89 (m, 2H), 3.85-3.78 (m, 1H), 3.49 (ddd, J=13.3, 8.0, 4.1 Hz, 1H), 2.07 (dddd, J=12.2, 8.5, 7.0, 5.6 Hz, 1H), 1.98-1.89 (m, 2H), 1.70 (ddt, J=12.2, 8.5, 7.0 Hz, 1H); $^{13}$C NMR (126 MHz, CDCl$_3$) δ 155.30, 141.28, 137.07, 129.62, 127.06, 125.80, 121.62, 118.27, 110.89, 77.87, 68.10, 45.62, 28.96, 25.95; GC/MS (CI$^+$, methane): m/z=229 (100%, M+H$^+$), 230 (17.6%), 257 (17.9%, M+C$_2$H$_9$$^+$), 199 (1%), 144 (4%).

Conjugate acid of ligand used in Ex. No. 211: $^1$H NMR (500 MHz, CDCl$_3$) δ 8.61 (s, 1H), 7.96 (d, J=5.9 Hz, 1H), 7.70 (d, J=8.3, 1H), 7.62 (d, J=8.1 Hz, 1H), 7.54 (dd, J=8.1, 6.9, 1H), 7.42 (dd, J=8.3, 6.9, 1H), 6.82 (d, J=5.9 Hz, 1H), 3.49 (d, J=4.1 Hz, 2H), 2.42 (s, 2H), 2.42 (s, 6H), 1.07 (s, 6H); $^{13}$C NMR (126 MHz, CDCl$_3$) δ 156.24, 141.84, 137.10, 129.31, 126.89, 125.48, 121.87, 118.78, 109.39, 71.88, 54.47, 48.52, 34.45, 25.56; GC/MS (CI$^+$, methane): m/z=258 (100%, M+H$^+$), 259 (19.1%), 286 (16.6%, M+C$_2$H$_9$$^+$), 213 (M-NHMe$_2$+H$^+$, 17.1%).

Conjugate acid of ligand used in Example 216: prepare N,N'-diphenylbenzamidine according to the procedure of Hontz A. C. and Wagner E. C., Organic Synthesis, 1951; 31:43 and Organic Synthesis, 1963, Collective Volume 4, page 383.

Examples 217 and 218 replicate Preparation 1 and Example 1 except use 2-methylaminoquinoline and N-([1,1'-biphenyl]-2-yl(6-(naphthalen-1-yl)pyridin-2-yl)methyl)-2,6-diisopropylaniline, respectively, instead of 2-benzylamino-6-methylpyridine to give complexes (6) and (7), respectively, of Examples 217 and 218, respectively:

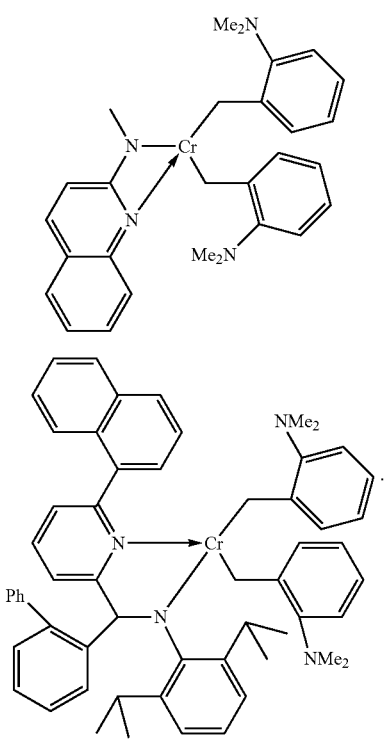

The complex of formula (7) of Example 218 employs the same ligand L as the complex of Example 30.

Example A general procedure for polymerization of propylene. Set up: conduct propylene polymerizations in a 1.8 L stainless steel batch reactor (Buchi AG) fitted with an agitator for stirring reactor contents and a bottom-located, large orifice bottom dump valve, which is used to empty reactor contents into a 6 L stainless steel dump pot vented to a 30 gal blow-down tank. The reactor can be heated or cooled via its vessel jacket and reactor head by circulating SYLTHERM™ 800 heat transfer fluid from a separate heating/cooling system controlled and monitored by a Camile TG process computer. Purge both the dump pot and blow-down tank with $N_2$ gas. Pass all chemicals used for polymerization or catalyst activation through purification columns to remove any impurities that may affect polymerization: pass propylene and toluene through 2 columns: the first containing A2 alumna and the second containing Q5 reactant. Pass $N_2$ gas through a single Q5 reactant column.

Polymerization run: set reactor temperature to 50° C. If Al-based scavengers (e.g., MMAO) are used, transfer them to a catalyst shot tank, and then to the reactor. Add mixed paraffinic alkanes (477 g, Isopar E™, ExxonMobil, Houston, Tex., USA) using a micro-motion flow-meter to accurately add the desired amount. Then add propylene (117 g), 1-butene, or other 1-alkene and, optionally ethylene, through the micro-motion flow-meter. Then heat reactor contents to 60° C. or other desired reaction temperature before conducting polymerization. In a separate container under $N_2$ gas atmosphere mix complex of formula (K) (e.g., complex of formula (K1)) obtained as dry powder from a sealed vial) with cocatalyst (preferably, MMAO, ferrocenium tetrakis(pentafluorophenyl)borate, BOMATPB, or a combination thereof) dissolved in toluene for 10 minutes to prepare a solution of the chromium catalyst, and transfer the chromium catalyst solution into the catalyst shot tank. Rinse container 3 times with toluene (5 mL each), and transfer rinses into the catalyst shot tank. (If a CSA (e.g., diethyl zinc (DEZ)) is used, add the CSA dissolved in solvent (preferably toluene) to the catalyst shot tank, and transfer the CSA solution to the reactor just before adding the chromium catalyst mixture to the catalyst shot tank.) Start polymerization run timer immediately after the addition of the chromium catalyst solution to the reactor. When the polymerization reaches a desired run time set point (e.g., 20 minutes), stop the agitator, pressure the reactor up to 500 psi with $N_2$ gas, and open the bottom dump valve to empty reactor contents to the dump pot. Pour the emptied contents from the dump pot into trays. Alternatively, pour the emptied contents from the dump pot into a 4 L beaker containing 2 L of MeOH and 100 mL concentrated aq. HCl. Stir beaker contents and then recover the PCS polypropylene polymer product by filtering the beaker contents. Rinse the filtercake with MeOH, and put in trays. Dry polymer product in trays in a vacuum oven at 140° C. under reduced pressure to remove any remaining solvent and other volatiles. Cool trays and contents to ambient temperature to give dried PCS polypropylene.

Differential scanning calorimetry (DSC): Determine melting and crystallization temperatures of the final product by DSC using a DSC model DSC 2910, TA Instruments, Inc. First heat samples from room temperature to 210° C. at first heating rate 10° C./minute. After holding at this temperature for 4 minutes, cool the samples to −40° C. at cooling rate 10° C./minutes, hold at −40° C. for 4 minutes, and then heat the sample to 215° C. at second heating rate 10° C./minutes.

Fourier Transform Infrared (FT-IR) Spectroscopy: Use a Nicolet Nexus 670 FT-IR ESP infrared spectrometer. Dissolve polymer sample in 1,2,4-trichlorobenzene (TCB) to give a concentration of 30 milligrams per milliliter (mg/mL) by shaking at 160° C. for 1 hour. Deposit the resulting 160° C. solution into individual cells on a silicon wafer, and evaporate TCB. Cool the residual polymer to room temperature, and analyze it to determine Mol % 1-octene residuals therein.

Gel permeation chromatography (GPC) Method: Use a GPC instrument (e.g., Viscotek Triple-Detection HT-GPC350 instrument with OmniSEC v4.6 software) using two (2) Polymer Labs PLgel 10 micron (μm) MIXED-B columns (300 millimeters (mm)×10 mm) at a flow rate of GPC mobile phase of 2.0 milliliters (mL) per minute (mL/min) at 150° C. and a PolyChar IR4 detector in concentration mode. Prepare the GPC mobile phase as 1,2,4-Trichlorobenzene (TCB) with 300 parts per million (ppm) butylated hydroxytoluene (BHT), which is supplied by Fisher Scientific, and previously distilled in-house and then filtered through 0.2 micron (μm) filters after dissolution of BHT stabilizer. Prepare all GPC samples by dissolving polymer in the GPC mobile phase by stirring for 90 minutes at 160° C. to give a concentration of 30 mg/mL, then dilute to a concentration of 1 mg/mL with additional GPC mobile phase. Inject a 400 microliter (μL) aliquot. Analyze samples for $M_w$ using a conventional calibration of narrow polystyrene (PS) standards with apparent units adjusted to homo-polyethylene (PE) using known Mark-Houwink coefficients for PS and PE in TCB at this temperature. Calculate absolute Mw information using a PDI static low-angle light scatter detector. Use a single 99,000 g/mol $M_w$ Polystyrene standard to calibrate the system for Triple-detection and determine $M_w$ and $M_n$.

$^1$H-NMR and $^{13}$C-NMR spectroscopy: prepare an analysis sample from a polyolefin sample by dissolving 0.4 g of the polyolefin sample in 1 g of 1,1,2,2-tetrachloroethane-$d_2$ containing Cr(acetylacetonate)$_3$ (0.025M) at 120° C. in a 5 millimeter (mm) NMR tube. Collect NMR data at 130° C. using a JEOL Eclipse™ 400 MHz or 500 MHz spectrometer or a Varian Unity Plus™ 400 MHz or 500 MHz spectrometer. Determine comonomer incorporation with $^{13}$C data using Randall's triad method (Randall, J. C.; JMS-Rev. Macromol. Chem. Phys., C29, 201-317 (1989).

Employ the analytical technique based on the ad rem method of US 2010/0093964 A1 on polyolefin products to determine they comprise OBCs and the OBCs have at least one of the aforementioned polymer characteristics (a) to (d). Find that the products contain at least diblocks. Determine the amount of OBC products, with the remainder being homopolymers (e.g., _PCS poly(1-alkene) and isotactic poly (1-alkene)). Determine that the ethylene residual repeat units predominantly end up in the PCS poly(1-alkene) atactic block and not in the syndiotactic or isotactic poly(1-alkene) block of the OBC.

Examples A1 to A210 perform the procedure of Example A a total of 210 times with propylene, each time using a different chromium complex of Examples 1 to 5 and 7 to 106 twice to give a chain straightened polypropylene or PCS PP/iPP/OBC blend of Examples A1 to A210.

Example B

General procedure for continuous solution polymerization of propylene. Carry out small scale continuous solution polymerizations out in a computer controlled 0.10 L autoclave reactor equipped with an internal stirrer and a single baffle. Purified mixed alkanes solvent (Isopar™ E available from ExxonMobil, Inc.), ethylene at 0.0126 lbs/hour (0.0057 kg/hour), and propylene at 0.113 lbs/hour (0.051 kg/hour) are supplied to the reactor equipped with a jacket for temperature control and an internal thermocouple. Maintain reactor temperature set point at 120° C. by circulating heated oil through the jacket. Feed all liquid components, solvent, catalyst, activator and chain shuttling agents into the reactor with syringe pumps. Use mass flow controllers to deliver propylene and ethylene to the reactor. Introduce feed streams of the components into the bottom of the reactor via two dip tubes. Run the reactor liquid-full at 400 psig (2.7 MPa) with vigorous stirring while removing the polymer product through an exit line at the top of the reactor. Pass the removed reactor effluent through an optical spectrometer cell monitoring exit stream composition as it exits the electrically heat traced and insulated system. Stop polymerization by the addition of a small amount of water and propanol into the exit line along with stabilizers and additives (e.g., 67 milligrams (mg) of a hindered phenol antioxidant (IRGANOX™ 1010 from Ciba Geigy Corporation) and 133 mg of a phosphorus stabilizer (IRGAFOS™ 168 from Ciba Geigy Corporation)). Collect polymer samples in open pans and dry in a temperature ramped vacuum oven for approximately 10 hours with a final high temperature set point of 140° C.-150° C. Characterize polymer product as described previously in Example A. If desired, determine percent olefin block copolymer (e.g., diblock, triblock, etc. olefin copolymer) versus non-block polymers (blend) in product based on the ad rem method of US 2010/0093964 A1.

Example B1 use the aforementioned SIOP-2b for the isotactic catalyst, the chromium complex (1) of Example 1, and TTB as cocatalyst in a molar ratio of 0.11/0/0.99/1.2 based on a feed rate of 0.23 mg per minute of the chromium complex (1) of Example 1. Run data: 100° C., 0.852 g propylene/minute feed rate (4000 g polymer/g Cr), 0.059 g ethylene/minute feed rate, 2.111 ppm diethyl zinc (g/g polymer), 16 wt % polymer solids in the reactor compared to weight of total polymerization mixture. Example B1 prepares an olefin block copolymer comprising an isotactic polypropylene (iPP) block (from SIOP-2b) and an atactic PCS polypropylene block (from (1)), the atactic PCS polypropylene block containing ethylene residuals therein, the atactic PCS polypropylene block is covalently bound to the iPP block. The measured $T_m$ compared to predicted $T_m$ indicates the iPP block has not been degraded, i.e., that a significant amount of ethylene has not been incorporated into the iPP block by the SIOP-2b, and thus (1) is selective for ethylene compared to SIOP-2b.

As shown by the Examples, the present invention has the uses and advantages described previously herein, especially those listed in the Brief Summary of the Present Invention.

What is claimed is:

1. A non-cyclopentadienyl-based chromium-ligand complex of formula (J): $LCr(R^A)_m(D)_k$ (J), wherein L is a non-Cp monoanionic ligand; Cr (chromium) is in a formal oxidation state of +3 or +2; when Cr formally is $Cr^{+3}$, either m is 1 and $R^A$ is hydrocarbylene (a hydrocarbylene chromium-ligand complex of formula (J)) or m is 2 and each $R^A$ independently is hydrocarbyl (a dihydrocarbyl chromium-ligand complex of formula (J)), wherein each hydrocarbyl or hydrocarbylene of $R^A$ independently is unsubstituted or substituted by from 1 to 5 $R^{AS}$; each $R^{AS}$ independently is a neutral aprotic heteroalkyl, neutral aprotic heterocycloalkyl, neutral aprotic heteroaryl, or neutral aprotic aryl; when Cr formally is $Cr^{+2}$, m is 1 and $R^A$ is hydrocarbyl (a hydrocarbyl chromium-ligand complex of formula (J)); k is an integer of 0 or 1; D is absent when k is 0 or D is a neutral ligand when k is 1; wherein the chromium-ligand complex of formula (J) is overall neutral and lacks a cyclopentadienyl-based (Cp-based) moiety, wherein k is 0; D is absent; and, wherein L is a conjugate base form of any one of the following compounds:

$N^1$-((1H-pyrrol-2-yl)methylene)-$N^2$,$N^2$-dimethylethane-1,2-diamine; diphenyl(pyridin-2-yl)methanol; N-(2-((benzylimino)methyl)phenyl)methanesulfonamide; N-((1H-pyrrol-2-yl)methylene)-2-methoxyethanamine; N-((1H-pyrrol-2-yl)methylene)-2-(methylthio)ethanamine; N-((1H-pyrrol-2-yl)methylene)-2-(benzylthio)ethanamine; $N^1$-((1H-indol-2-yl) methylene)-$N^2$,$N^2$-dimethylethane-1,2-diamine; N-((1H-pyrrol-2-yl)methylene)-2-(diphenylphosphino) ethanamine; N-((1H-pyrrol-2-yl)methylene)-2-(di(propan-2-yl)phosphino)ethanamine; N-((1H-pyrrol-2-yl) methylene)-2-(pyrrolidin-1-yl)ethanamine; N-((1H-pyrrol-2-yl)methylene)-2-(piperidin-1-yl)ethanamine; N-methylisoquinolin-1-amine; 2,6-di(propan-2-yl)-N-((6-(naphthalen-1-yl)pyridin-2-yl)methylene)aniline; 4-chloro-N-((6-(4-chlorophenyl)pyridin-2-yl)methylene)-2,6-di(propan-2-yl)aniline; 3-((pyridin-2-ylmethyl)amino)butan-2-one oxime; 4-methyl-N-(2-0(4-methylphenyl)imino)methyl)phenyl)-benzenesulfonamide; N-(2-((butylimino)methyl) phenyl)-4-methylbenzenesulfonamide; N-(2-((benzylimino)methyl)phenyl)-4-methylbenzenesulfonamide; N-(2-((benzylimino) methyl)phenyl)-2,4,6-tri(propan-2-yl) benzenesulfonamide; 9-(4-methoxypyrimidin-5-yl)-9H-xanthen-9-ol; bis(4-methoxypyrimidin-5-yl) (phenyl)methanol; bis(4-ethoxypyrimidin-5-yl) (phenyl)methanol; 1-(2-ethoxy-6-methoxyphenyl)-2- methyl-1-phenylpropan-1-ol; N-([1,1'-biphenyl]-2-yl (6-naphthalen-1-yl)pyridin-2-yl)methyl-2,6-di(propan-2-yl)aniline; N-benzyl-6-methylpyridin-2-amine; $N^1$-(isoquinolin-1-yl)-$N^2,N^2$-dimethylethane-1,2-diamine; N-(2-methoxyethyl)isoquinolin-1-amine; $N^1$-(isoquinolin-1-yl)-$N^3,N^3$-dimethylpropane-1,3-diamine; N-((tetrahydrofuran-2-yl)methyl)isoquinolin-1-amine; $N^1$-(isoquinolin-1-yl)-$N^3,N^3$,2,2-tetramethylpropane-1,3-diamine; 2,3-dihydro-1H-pyrrolo[2,3-b]pyridine; N-(furan-2-ylmethyl)isoquinolin-1-amine; 1,2-dihydropyrrolo[4,3,2-ij]isoquinoline; 2,3-dihydro-1H-benzo[de][1,8]naphthyridine; and N,N'-diphenylbenzamidine.

2. The complex as in claim 1, wherein m is 2 and each $R^A$ is methyl or benzyl.

3. A non-cyclopentadienyl-based chromium-ligand complex, wherein the complex is any one of complexes (1) to (7):

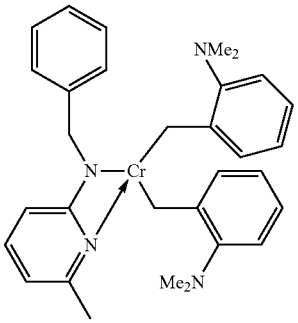

(1)

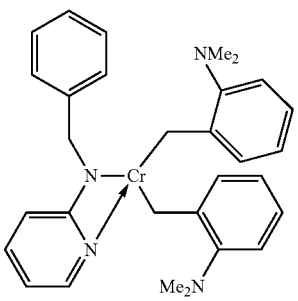

(2)

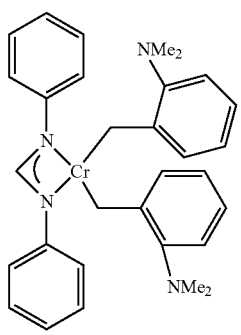

(3)

-continued

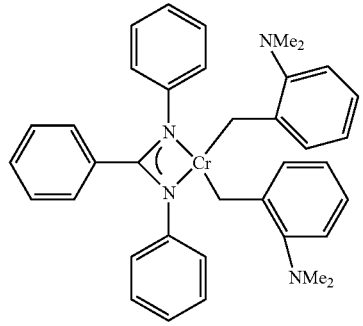

(4)

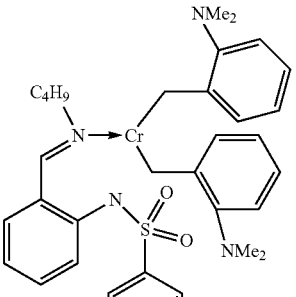

(5)

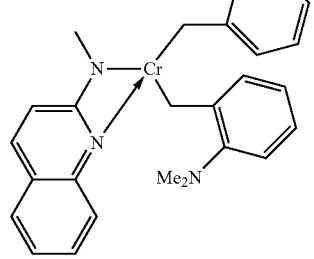

(6)

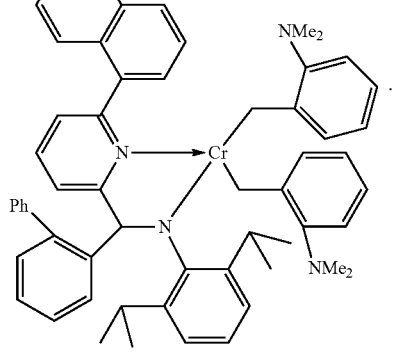

(7)

4. A chromium catalyst useful for polymerizing an olefin monomer, the chromium catalyst comprising a mixture or reaction product of the complex of any one of complexes (1) to (7) as in claim 3 and an activating cocatalyst, wherein the ratio of total number of moles of the complex of any one of complexes (1) to (7) to total number of moles of the activating cocatalyst is from 1:10,000 to 100:1.

* * * * *